United States Patent
Van Antwerp et al.

(10) Patent No.: US 9,623,085 B2
(45) Date of Patent: Apr. 18, 2017

(54) CHIMERIC NATRIURETIC PEPTIDE COMPOSITIONS AND METHODS OF PREPARATION

(71) Applicant: Capricor Therapeutics, Inc., Beverly Hills, CA (US)

(72) Inventors: William Van Antwerp, Valencia, CA (US); Andrew J. L. Walsh, Minneapolis, MN (US); Lian Luo, Plymouth, MN (US); Dianne L. Judd, Minneapolis, MN (US)

(73) Assignee: Capricor Therapeutics, Inc., Beverly Hills, CA (US)

( * ) Notice: Subject to any disclaimer, the term of this patent is extended or adjusted under 35 U.S.C. 154(b) by 0 days.

(21) Appl. No.: 14/934,617

(22) Filed: Nov. 6, 2015

(65) Prior Publication Data

US 2016/0051632 A1 Feb. 25, 2016

Related U.S. Application Data

(63) Continuation of application No. 13/602,187, filed on Sep. 2, 2012, now abandoned.

(60) Provisional application No. 61/530,920, filed on Sep. 2, 2011.

(51) Int. Cl.
| | | |
|---|---|---|
| *A61K 38/00* | (2006.01) | |
| *A61K 38/12* | (2006.01) | |
| *A61K 38/22* | (2006.01) | |
| *C07K 14/58* | (2006.01) | |
| *A61K 9/00* | (2006.01) | |
| *A61K 47/02* | (2006.01) | |
| *A61K 47/10* | (2017.01) | |
| *A61K 47/18* | (2017.01) | |
| *A61K 9/08* | (2006.01) | |

(52) U.S. Cl.
CPC ........ *A61K 38/2242* (2013.01); *A61K 9/0019* (2013.01); *A61K 9/08* (2013.01); *A61K 38/22* (2013.01); *A61K 47/02* (2013.01); *A61K 47/10* (2013.01); *A61K 47/18* (2013.01); *C07K 14/58* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,508,712 A | 4/1985 | Needleman | |
| 4,562,751 A | 1/1986 | Nason et al. | |
| 4,569,641 A | 2/1986 | Falk et al. | |
| 4,685,903 A | 8/1987 | Cable et al. | |
| 4,728,044 A | 3/1988 | Duill et al. | |
| 4,751,284 A | 6/1988 | Forsmann | |
| 4,761,469 A | 8/1988 | de Bold | |
| 4,764,504 A | 8/1988 | Johnson et al. | |
| 4,851,349 A | 7/1989 | Nakanishi et al. | |
| 4,883,467 A | 11/1989 | Franetzki et al. | |
| 4,895,932 A | 1/1990 | Forssmann | |
| 5,080,653 A | 1/1992 | Voss et al. | |
| 5,097,122 A | 3/1992 | Colman et al. | |
| 5,135,912 A | 8/1992 | Wiedemann et al. | |
| 5,202,239 A | 4/1993 | Tarnowski et al. | |
| 5,212,286 A | 5/1993 | Lewicki et al. | |
| 5,395,340 A | 3/1995 | Lee | |
| 5,505,709 A | 4/1996 | Funderburk et al. | |
| 5,665,704 A | 9/1997 | Lowe et al. | |
| 5,691,310 A | 11/1997 | Vesely | |
| 5,846,932 A | 12/1998 | Lowe et al. | |
| 5,948,761 A | 9/1999 | Seilhamer et al. | |
| 6,136,564 A | 10/2000 | Kopetzki | |
| 6,372,499 B1 | 4/2002 | Midoux et al. | |
| 6,407,211 B1* | 6/2002 | Burnett, Jr. ............ | C07K 14/58 435/7.1 |
| 6,423,035 B1 | 7/2002 | Das et al. | |
| 6,525,022 B1 | 2/2003 | Lowe et al. | |
| 6,541,939 B2 | 4/2003 | Kishibe et al. | |
| 6,551,276 B1 | 4/2003 | Mann et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |

(Continued)

FOREIGN PATENT DOCUMENTS

| | | |
|---|---|---|
| EP | 0180615 B1 | 4/1986 |
| EP | 0465097 A2 | 1/1992 |

(Continued)

OTHER PUBLICATIONS

Abd-Elsalam et al. 2011. "What is the Optimum Concentration of m-cresol in antivenoms?" J. Venomous Animals and Toxins, ISSN 1678-9199, vol. 17(1) :12-22.
Brenner et al., 1990. "Diverse Biological Actions of Atrial Natriuretic Peptide," Physiol. Rev., 70(3):665-669.
Burton et al., 2009. Hemodialysis-Induced Cardiac Injury: Determinants and Outcomes, Clinical J.A. Society Nephrol., 4:914-920.
Chen H.H., 2000. Subcutaneous Administration of Brain Natriuretic Peptide in Experimental Heart Failure, J. of American College of Cardiology, 36 (5):1706-1712, Jun. 19, 2000.

(Continued)

*Primary Examiner* — Shulamith H Shafer
(74) *Attorney, Agent, or Firm* — Knowles IP Strategies, LLC

(57) ABSTRACT

Therapeutic compositions containing chimeric natriuretic peptides for treating chronic kidney disease alone, heart failure alone, or chronic kidney disease with concomitant heart failure are described. The therapeutic compositions have enhanced stability characteristics to facilitate storage and delivery by provisioning apparatuses under conditions of elevated temperature and mechanical stress. Methods for increasing the stability of therapeutic compositions containing chimeric natriuretic peptides are further described.

13 Claims, 3 Drawing Sheets

(56) References Cited

U.S. PATENT DOCUMENTS

| | | | |
|---|---|---|---|
| 6,629,954 B1 | 10/2003 | Heruth | |
| 6,641,533 B2 | 11/2003 | Causey, III et al. | |
| 6,652,493 B1 | 11/2003 | Das | |
| 6,656,148 B2 | 12/2003 | Das et al. | |
| 6,659,980 B2 | 12/2003 | Maberg et al. | |
| 6,752,787 B1 | 6/2004 | Causey, III et al. | |
| 6,800,071 B1 | 10/2004 | McConnell et al. | |
| 6,817,990 B2 | 11/2004 | Yap et al. | |
| 6,833,358 B1 | 12/2004 | Nakata et al. | |
| 6,849,714 B1 | 2/2005 | Bridon et al. | |
| 6,872,200 B2 | 3/2005 | Gray et al. | |
| 6,887,470 B1 | 5/2005 | Bridon et al. | |
| 6,897,030 B2 | 5/2005 | Seilhamer et al. | |
| 6,932,584 B2 | 8/2005 | Gray et al. | |
| 6,936,029 B2 | 8/2005 | Mann et al. | |
| 6,974,861 B2 | 12/2005 | Seilhamer et al. | |
| 6,979,326 B2 | 12/2005 | Mann et al. | |
| 6,997,920 B2 | 2/2006 | Mann et al. | |
| 7,025,743 B2 | 4/2006 | Mann et al. | |
| 7,026,293 B2 | 4/2006 | Kitakaze | |
| 7,033,997 B2 | 4/2006 | Forssmann et al. | |
| 7,179,790 B2 | 2/2007 | Seilhamer et al. | |
| 7,256,253 B2 | 8/2007 | Bridon et al. | |
| 7,276,481 B2 | 10/2007 | Golembo et al. | |
| 7,288,085 B2 | 10/2007 | Olsen | |
| 7,341,838 B2 | 3/2008 | Buechler et al. | |
| 7,384,917 B2 | 6/2008 | Burnett, Jr. et al. | |
| 7,414,107 B2 | 8/2008 | Larsen | |
| 7,569,384 B2 | 8/2009 | Rosen et al. | |
| 7,585,837 B2 | 9/2009 | Shechter et al. | |
| 7,642,243 B2 | 1/2010 | Nakao et al. | |
| 7,648,962 B2 | 1/2010 | James et al. | |
| 7,655,772 B2 | 2/2010 | Mohapatra | |
| 7,662,773 B2 | 2/2010 | James et al. | |
| 7,714,100 B2 | 5/2010 | Cohen et al. | |
| 7,754,852 B2 * | 7/2010 | Burnett, Jr. | C07K 14/58 530/324 |
| 7,917,208 B2 | 3/2011 | Yomtov et al. | |
| 8,455,438 B2 | 6/2013 | Burnett, Jr. et al. | |
| 8,501,693 B2 | 8/2013 | Kim et al. | |
| 2002/0082219 A1 | 6/2002 | Burnett, Jr. et al. | |
| 2003/0069186 A1 | 4/2003 | Burnett, Jr. et al. | |
| 2004/0053245 A1 | 3/2004 | Tang et al. | |
| 2004/0077537 A1 | 4/2004 | Schreiner | |
| 2004/0106953 A1 | 6/2004 | Yomtov et al. | |
| 2004/0138134 A1 | 7/2004 | Golembo | |
| 2004/0176914 A1 | 9/2004 | Buechler et al. | |
| 2004/0203081 A1 | 10/2004 | James et al. | |
| 2005/0059600 A1 | 3/2005 | Burnett, Jr. et al. | |
| 2005/0064511 A1 | 3/2005 | Buechler et al. | |
| 2005/0065760 A1 | 3/2005 | Murtfeldt et al. | |
| 2005/0106592 A1 | 5/2005 | Schleuning et al. | |
| 2005/0113286 A1 | 5/2005 | Schreiner et al. | |
| 2005/0232981 A1 | 10/2005 | Ben-Sasson | |
| 2005/0244904 A1 | 11/2005 | Ng | |
| 2005/0272650 A1 | 12/2005 | Mohapatra | |
| 2006/0025367 A1 | 2/2006 | Simari | |
| 2006/0052764 A1 | 3/2006 | Gelfand et al. | |
| 2006/0074009 A1 | 4/2006 | James et al. | |
| 2006/0110359 A1 | 5/2006 | Sanchez-Ramos et al. | |
| 2006/0172933 A1 | 8/2006 | James et al. | |
| 2006/0205642 A1 | 9/2006 | Vesely | |
| 2006/0264376 A1 | 11/2006 | Mitrovic et al. | |
| 2006/0276382 A1 | 12/2006 | Mohapatra | |
| 2007/0027306 A1 | 2/2007 | Rosen et al. | |
| 2007/0042957 A1 | 2/2007 | Burnett, Jr. et al. | |
| 2007/0048282 A1 | 3/2007 | Rosen et al. | |
| 2007/0197434 A1 | 8/2007 | Nakao et al. | |
| 2008/0004206 A1 | 1/2008 | Rosen et al. | |
| 2008/0015152 A1 | 1/2008 | Larsen | |
| 2008/0032933 A1 | 2/2008 | Burnett, Jr. et al. | |
| 2008/0039394 A1 | 2/2008 | Vesely | |
| 2008/0051716 A1 | 2/2008 | Stutz | |
| 2008/0070858 A1 | 3/2008 | Mohapatra | |
| 2008/0139785 A1 | 6/2008 | Larsen | |
| 2008/0153747 A1 | 6/2008 | Alewood | |
| 2008/0163747 A1 | 7/2008 | Uehara et al. | |
| 2008/0188796 A1 | 8/2008 | Steil et al. | |
| 2008/0194481 A1 | 8/2008 | Rosen et al. | |
| 2008/0194682 A1 | 8/2008 | Golembo et al. | |
| 2008/0207505 A1 | 8/2008 | James | |
| 2008/0214437 A1 | 9/2008 | Mohapatra et al. | |
| 2008/0227954 A1 | 9/2008 | Larsen | |
| 2008/0234467 A1 | 9/2008 | Larsen | |
| 2008/0312142 A1 | 12/2008 | Nakao et al. | |
| 2008/0312157 A1 | 12/2008 | Levy et al. | |
| 2009/0011997 A1 | 1/2009 | Peri et al. | |
| 2009/0035287 A1 | 2/2009 | Levine et al. | |
| 2009/0036364 A1 | 2/2009 | Levy et al. | |
| 2009/0062206 A1 | 3/2009 | Vesely | |
| 2009/0062730 A1 | 3/2009 | Woo | |
| 2009/0069243 A1 | 3/2009 | Burnett, Jr. et al. | |
| 2009/0093408 A1 | 4/2009 | Bridon et al. | |
| 2009/0170196 A1 | 7/2009 | Vesely | |
| 2009/0170756 A1 | 7/2009 | Burnett, Jr. et al. | |
| 2009/0175821 A1 | 7/2009 | Bridon et al. | |
| 2009/0176706 A1 | 7/2009 | Mohapatra | |
| 2009/0247462 A1 | 10/2009 | Bogin et al. | |
| 2009/0281528 A1 | 11/2009 | Grovender et al. | |
| 2009/0286723 A1 | 11/2009 | Levy et al. | |
| 2009/0287267 A1 | 11/2009 | Wenzel et al. | |
| 2010/0010330 A1 | 1/2010 | Rankers et al. | |
| 2010/0028372 A1 | 2/2010 | Jezek | |
| 2010/0055150 A1 | 3/2010 | Golembo et al. | |
| 2010/0093627 A1 | 4/2010 | Rosen et al. | |
| 2010/0204094 A1 | 8/2010 | Simari et al. | |
| 2010/0204109 A1 | 8/2010 | Bevec | |
| 2010/0216714 A1 | 8/2010 | James et al. | |
| 2010/0297021 A1 | 11/2010 | Wendt et al. | |
| 2010/0298901 A1 | 11/2010 | Sommer et al. | |
| 2011/0034386 A1 | 2/2011 | Vesely | |
| 2011/0152194 A1 | 6/2011 | Burnett, Jr. et al. | |
| 2011/0206633 A1 | 8/2011 | Bossard | |
| 2011/0282030 A1 * | 11/2011 | Dickey | C07K 14/58 530/324 |
| 2012/0178689 A1 | 7/2012 | Evans et al. | |
| 2012/0220528 A1 | 8/2012 | Van Antwerp et al. | |
| 2012/0277155 A1 | 11/2012 | VanAntwerp et al. | |
| 2013/0244937 A1 | 9/2013 | Van Antwerp et al. | |
| 2013/0274705 A1 | 10/2013 | Burnes et al. | |
| 2014/0031787 A1 | 1/2014 | Burnes et al. | |
| 2015/0038418 A1 | 2/2015 | Van Antwerp et al. | |

FOREIGN PATENT DOCUMENTS

| | | |
|---|---|---|
| EP | 0792270 B1 | 9/1997 |
| EP | 1242452 B1 | 9/2002 |
| EP | 1569683 B1 | 9/2005 |
| EP | 1656555 B1 | 5/2006 |
| EP | 1773867 B1 | 4/2007 |
| EP | 1865976 B1 | 12/2007 |
| WO | 01/44284 A2 | 6/2001 |
| WO | 01/70307 A1 | 9/2001 |
| WO | 03/079979 A2 | 10/2003 |
| WO | 2004/030716 A2 | 4/2004 |
| WO | 2004/030717 A2 | 4/2004 |
| WO | 2005/094420 A1 | 10/2005 |
| WO | 2005/116655 A2 | 12/2005 |
| WO | 2007/047504 A2 | 4/2007 |
| WO | 2008/021872 A1 | 2/2008 |
| WO | 2008/031045 A2 | 3/2008 |
| WO | 2008/079995 A2 | 7/2008 |
| WO | 2009/033724 A1 | 3/2009 |
| WO | 2009/033807 A2 | 3/2009 |
| WO | 2009/040024 A2 | 4/2009 |
| WO | 2009/040031 A2 | 4/2009 |
| WO | 2009/046861 A1 | 4/2009 |
| WO | 2009/149161 A2 | 12/2009 |
| WO | 2010/033217 A1 | 3/2010 |
| WO | 2010/048308 A2 | 4/2010 |
| WO | 2010/063124 A1 | 6/2010 |
| WO | 2010/078325 A2 | 7/2010 |
| WO | 2012/058585 A2 | 5/2012 |
| WO | 2012/115771 A2 | 8/2012 |

(56) References Cited

FOREIGN PATENT DOCUMENTS

| WO | 2013/016148 A2 | 1/2013 |
|---|---|---|
| WO | 2013/019237 A1 | 2/2013 |
| WO | 2013/033675 A1 | 3/2013 |

OTHER PUBLICATIONS

Chung, Eugene S., et al., 2006. "Safety and Tolerability of Serial Home Infusions of Nesiritide for Advanced Heart Failure", Am. J. Cardiol vol. 97:1370-1373.
Clemens et al. 1998. "Pharmacokinetics and Biological Actions of Subcutaneously Administered Human Brain Natriuretic Peptide", J. Pharm Exp Therap. 287 (1):67-71.
DeBold et al., 1981 "A Rapid and Potent Natriuretic Response to Intravenous Injection of Atrial Myocardial Extract in Rats," Life Sciences, 28(1):89-94.
Evans, Nile Therapeutics Press Release Oct. 14, 2008.
International Search Report of PCT/US2012/024203, mailed Nov. 22, 2012.
International Search Report PCT/US2012/047492, mailed Jan. 29, 2013.
Jong et al., 2002. "Prognosis and Determinants of Newly Hospitalized for Heart Failure: A Population Based Study", Arch. Intern. Med., 162:1689-1694.
Kozak et al., 2005. National Hospital Discharge Survey: 2002 Annual Summary With Detailed Diagnosis and Procedure Data, Vital Health Stat. 13, 158:1-199.
Lieu, et al., 2009. "Initial Observations of Intravenous CD-NP, Chimeric Natriuetic Peptide, on Renal Functions in chronic Heart Failure Patients," Journal of Cardiac Failure, 15 (6):S77, Aug. 2009.
Lingegowda et al., 2010. "Long-term Outcome of Patients Treated with Prophylactic Mesiritide for the Prevention of Acute Kidney Injury following Cardiovascular Surgery," Clinical Cardiol., 33(4):217-221.
Lisy, 0., et al. 2008. Design, Synthesis, and Actions of a Novel Chimeric Natriuretic Peptide: CD-NP, J. American College of Cardiology, 52(1) :60-68.
McCullough et al., 2008. "Chronic Kidney Diseases, Prevalence of Premature Cardiovascular Disease, and Relationship to Short-term Mortality," American Heart Journal, 156(2) :277-283, Abstract.
Meyer et al., 1998, "Urinary and Plasma Urodilatin Measured by a Direct RIA using a Highly Specific Antiserum," Clinical Chemistry, 44(12): pp. 2524-2529.
PCT/US2012/053578, International Search Report, Jan. 29, 2013.
PCT/US2013/032700, International Search Report, Jul. 15, 2013.
Perkins et al. 2000. Chapter 21 in Handbook of Pre-Clinical Continuous Intravenous Infusion, ed. Smith and Healing, Taylor and Francis, London).
Redfield et al. 1989, "Restoration of renal response to atria! natriuretic factor in experimental low-output heat failure", Am. J. Physiol, R917-923: 257.
Riter, et al., 2006. "Nonhypotensive Low-Dose Nesiritide has Differential Renal Effects Compared with Standard-Dose Nesiritide in Patients with Acute Decompensated Heart Failure and Renal Dysfunction", Jrnl ACC, vol. 47(11 ): 2334-2335.
Ronco et al., 2008, "Cardiorenal Syndrome", J. Am. Coll. Cardiol., 1527-1539:52.
Schirger 2011.Safety Study of Chimeric Natriuretic Peptide(CD-NP) in Stable LVAD Patients (NCT ID:NCT01750905). Published at www.mayo.edu/research/ clinical-trials/cls-20112083.
Search Report of EP application EP11793526.2, mailed Aug. 7, 2013.
Vesely et al. 1998. "Vessel Dilator Enhances Sodium and Water Excretion and has Beneficial Hemodynamic Effects in Persons with Congestive Heart Failure", Circulation, 98:323-329.
Vesely et al. 2000. "Long-Acting Natriuretic Peptide, Vessle Dilator, and Kaliuretic Peptide Enhance the Urinary Excretion Rate of 22—Microglobulin", Metabolism 49:1592-7.
Vesely et al. 2006. "Urodilatin and four cardiac hormones decrease human renal carcinoma cell numbers," European Journal of Clinical Investigation. vol. 36, pp. 810-819.

\* cited by examiner

CHIMERIC NATRIURETIC PEPTIDE COMPOSITIONS AND METHODS OF PREPARATION

CROSS-REFERENCE TO RELATED APPLICATIONS

This application is a continuation of U.S. patent application Ser. No. 13/602,187 filed Sep. 2, 2012, which claims priority to U.S. Provisional Application No. 61/530,920, filed on Sep. 2, 2011. The entirety of each of these applications is hereby incorporated by reference for all purposes.

REFERENCE TO SEQUENCE LISTING

The Sequence Listing associated with this application is provided in text format in lieu of a paper copy, and is hereby incorporated by reference into the specification. The name of the text file containing the Sequence Listing is 12011-005US2_2015-11-06_SequenceListing_ST25.txt. The text file is 5 KB, was created on Nov. 5, 2015, and is being submitted electronically via EFS-Web. The Sequence Listings accompanying U.S. application Ser. No. 13/602,187 filed on Sep. 2, 2012 and U.S. Provisional Application No. 61/530,920 filed on Sep. 2, 2011 are also incorporated by reference.

FIELD OF THE INVENTION

The invention relates to stable compositions for the administration of chimeric natriuretic peptides used in the treatment of pathological conditions such as chronic kidney disease alone, heart failure alone, or with concomitant chronic kidney disease and heart failure. Methods for preparing the stable compositions and use thereof are also provided.

BACKGROUND OF THE INVENTION

Proteins and peptides serve multifunctional roles in biological systems. As ligands for various receptors as well as substrates for various enzymes, peptides can be used to regulate biological processes wherein the function of proteins and peptides can be defined by the structure, orientation and positioning of side-chains in aqueous solution as determined by secondary and tertiary structure. However, the primary sequence of amino acid residues needed for proper orientation in aqueous solution can sometimes lead to instability. Due to the difficulties in delivering peptide-based drugs, relatively few peptide-based drugs are on the market. Although insulin and insulin derivatives are one of the first commercially formulated peptide based drugs, insulin has several structural features allowing for insulin to remain stable during long storage periods in solution compared with small peptides and particularly compared with small peptides synthesized through solid-phase synthesis rather than recombinant methods expressed inside a living cell. Without being limited to any one theory, human insulin, including human insulin recombinantly expressed in bacterial cells, is formed of two separate peptide chains having 21 and 30 amino acid residues, respectively. The two peptide chains are linked through three disulfide bridges between pairs of cysteine residues. Both peptide chains form a significant amount of alpha-helical secondary structure. Due to the disulfide bridges linking the peptide chains, the alpha-helical regions of the two peptide chains contact one another forming numerous salt bridges and van der Waals contacts. As a result, insulin has a well-ordered tertiary structure that stabilizes insulin against surface adsorption by reducing the exposure of hydrophobic regions to a surrounding aqueous environment. Further, the structure of insulin reduces mobility of the peptide backbone helping to protect insulin from proteolytic attack from acids or bases. Insulin in solution can form hexamers mediated by zinc ions, which further stabilize its structures. Many commercial formulations of insulin contain zinc salts to promote stability.

Natriuretic peptides have a structure allowing for the binding to atrial natriuretic peptide (ANP) receptor, which controls the activity of an associated guanylyl cyclase. The binding of an agonist ligand to the ANP receptor results in several physiological effects including decrease in cardiac volume and blood output, decrease in blood pressure and increase in glomerular filtration rate (GFR). Without being limited to any single theory, the natriuretic peptides are not believed to have significant amounts of secondary structure, such as alpha-helices. A lack of well-ordered secondary structure may possibly allow for a high degree of freedom of movement in the peptide chain, which can open the peptide chain to attack by proteolytic enzymes and acid/base attack as well as other chemical reactions such as deamidation. Hence, certain peptides and polypeptides, such as natriuretic peptides, may be rapidly degraded when formulated into a solution for administration. In particular, the amide bonds forming the peptide backbone can be subject to nucleophilic attack and hydrolysis in aqueous solutions. Further, peptides can be degraded by peptidases, amidases, and/or esterases present in the environment.

Stable formulations of therapeutic agents are particularly important for use in delivery devices that expose peptides to elevated temperatures, mechanical stress and/or hydrophobic interactions with components of delivery devices. Formulations of peptides should remain soluble and substantially free of aggregation, even though subjected to the subject's body heat and motion for periods ranging from a few days to several months. Of the 20 amino acids that form most natural peptide sequences, many have side chains that are hydrophobic, where peptides containing a high amount of such hydrophobic amino acid residues may have limited solubility in aqueous solution or undergo aggregation over time. For this reason, some peptides may have limited therapeutic use. Even in situations where a peptide has pharmacological effect when administered, the concentration of the peptide in an aqueous pharmaceutical composition can be unstable. Depending on the particular administration requirements and time limitations, a formulation with a short shelf-life may have little practical value. While organic solvents increase the solubility of most peptides, the presence of organic solvents in compositions for injection can be problematic. Chemical modifications of peptides to increase solubility are also known. Such chemical modifications can take the form of substitution of specific amino acid residues as well as covalent attachment to the N- and/or C-terminus of groups serving to increase solubility. However, without being limited to any particular theory, chemical modification can undesirably decrease the biological efficacy of the peptide. Hence, there is a need for a stable formulation of one or more chimeric natriuretic peptides having a long-shelf life that can be stably used in mechanical delivery or implantable devices for protracted periods of time. There is also a need for a method for preparing such stable chimeric natriuretic peptide formulations.

SUMMARY OF THE INVENTION

The disclosure provided herein is directed to compositions for stabilizing aqueous solutions containing chimeric natriuretic peptides during storage and administration to a subject and methods for preparing such stabilized solutions. The invention disclosed herein has a number of embodiments that relate to therapeutic methods and compositions for treatment of Chronic Kidney Disease (CKD) alone, Heart Failure (HF) alone or with concomitant CKD and HF.

The systems and methods of the invention are directed toward a stable therapeutic protein composition having one or more chimeric natriuretic peptides. The therapeutic protein composition can be administered to a subject for the treatment of CKD alone, HF alone or with concomitant CKD and HF. The systems, therapeutic protein compositions, and methods of the invention are also useful for treating other renal or cardiovascular diseases, such as congestive heart failure (CHF), dyspnea, elevated pulmonary capillary wedge pressure, chronic renal insufficiency, acute renal failure, cardiorenal syndrome, contrast induced nephropathy (CIN) and diabetes mellitus. The therapeutic protein compositions can be used for chronic and acute delivery through mutes of administration including but not limited to subcutaneous, intravascular, intraperitoneal, and direct to organ. One preferred route of the therapeutic protein compositions is subcutaneous administration. In certain embodiments, the therapeutic protein compositions can be delivered by implanted and external pumps at programmed or fixed rates, implanted or percutaneous vascular access ports, depot injection, direct delivery catheter systems, and local controlled release technology. It is understood that the disclosed list of devices for delivering the stable therapeutic protein compositions is non-exhaustive and that the compositions can be delivered by other suitable means known by those of skill in the art.

In any embodiment, a therapeutic protein composition contains one or more chimeric natriuretic peptide selected from CD-NP and CU-NP, about 0.15% to about 0.315% of m-cresol by weight (3-methylphenol), tris(hydroxymethyl)aminomethane, and water. The pH of the therapeutic protein composition can be from about 6.5 to 7.6.

In any embodiment, a therapeutic protein composition contains one or more chimeric natriuretic peptide selected from the group consisting of CD-NP and CU-NP, from about 0.2 to 10 grams per liter of phosphate buffer, from about 2 to about 15 grams per liter of sodium chloride, and water.

In any embodiment, a therapeutic protein composition has a pH from about 6.5 to 7.6.

In any embodiment, a therapeutic protein composition has a pH from about 6.5 to 7.6 when the therapeutic protein composition is adjusted at a temperature of 25° C.

In any embodiment, a concentration of tris(hydroxymethyl)aminomethane in the therapeutic protein composition is from about 5 to about 200 mM, from about 5 to about 100 mM or from about 10 to about 70 mM.

In any embodiment, a protein composition further comprises from about 0.1 to about 5% glycerol by weight.

In any embodiment, a therapeutic protein composition is stored in a container such as glass. The therapeutic protein composition contains one or more chimeric natriuretic peptide selected from CD-NP and CU-NP, about 0.15% to about 0.315% of m-cresol by weight, and an aqueous tris(hydroxymethyl)aminomethane buffer. The therapeutic protein composition can be administered and metered to a subject using a pump or drug provisioning apparatus. In any embodiment of the invention, the drug provisioning apparatus may administer the therapeutic protein composition to the subject subcutaneously, intramuscularly, or intravenously. The drug provisioning apparatus can consist of any of an external or implantable drug delivery pump, an implanted, subcutaneous, or percutaneous vascular access port, a direct delivery catheter system, and a local drug-release device.

In any embodiment, a therapeutic protein composition contains aqueous tris (hydroxymethyl)aminomethane, and about 0.15% to about 0.315% of m-cresol by weight. The protein composition can be formed at least 3 days prior to administration of the protein composition to a subject.

In any embodiment, a therapeutic protein composition is stored in a container for a time period of at least 3 days and the amount of a protein, polypeptide or peptide present in the composition after 3 days is about 80% or more of the amount of the protein, polypeptide or peptide comprised in the therapeutic protein composition prior to storage in the container for 3 days.

In any embodiment, a therapeutic protein composition is stored at a temperature from about 25 to about 45° C.

In any embodiment, a method for stabilizing a protein, peptide or polypeptide in solution has the steps dissolving a protein, peptide or polypeptide in a buffer composition comprising tris(hydroxymethyl)aminomethane, meta-cresol, glycerol and water to form a therapeutic protein composition.

In any embodiment, a therapeutic protein composition has a concentration of tris(hydroxymethyl)aminomethane from about 10 to about 75 mM.

In any embodiment, a therapeutic protein composition has a concentration of tris(hydroxymethyl)aminomethane from about 10 to about 100 mM.

In any embodiment, a therapeutic protein composition has a concentration of tris(hydroxymethyl)aminomethane from about 5 to about 100 mM.

In any embodiment, a therapeutic protein composition has from about 0.5 to about 2% glycerol by weight.

In any embodiment, a therapeutic protein composition has from about 0.1 to about 5% glycerol by weight.

In any embodiment, a therapeutic protein composition contains tris(hydroxymethyl)aminomethane, meta-cresol at a concentration of about 0.25% by weight, and glycerol at a concentration of about 1.6% by weight and has a pH of about 7.3.

In any embodiment, a therapeutic protein composition has a concentration from about 0.05 to about 20 mg/mL of a peptide.

In any embodiment, a therapeutic protein composition contains meta-cresol at a concentration from about 0.15 to about 0.315% by weight.

In any embodiment, a therapeutic protein composition has concentration of sodium chloride from about 0.2 to about 10 grams per liter.

In any embodiment, a therapeutic protein composition has concentration of sodium chloride from about 2 to about 15 grams per liter.

In any embodiment, a therapeutic protein composition has a concentration of phosphate buffer from about 0.2 to about 10 grams per liter.

In any embodiment, a therapeutic protein composition contains a peptide having at least about 20 amino acid residues.

In any embodiment, a therapeutic protein composition contains a peptide having an intramolecular disulfide bond between two cysteine amino acid residues.

In any embodiment, a therapeutic protein composition contains a peptide having an intramolecular disulfide bond between two cysteine amino acid residue and 15 amino acid residues between the two cysteine residues forming the disulfide bond.

In any embodiment, a therapeutic protein composition is stored in a container or vessel having a headspace purged with nitrogen or a noble gas to substantially remove oxygen from the headspace of the container.

In any embodiment, a therapeutic protein composition is formed with a degassed medium.

In any embodiment, a therapeutic protein composition is stored in a container at a temperature from about 25 to about 45° C. for a period of 3 days or more.

In any embodiment, a therapeutic protein composition is stored in a container that is glass.

In any embodiment, a therapeutic protein composition is stored in a provisioning apparatus and delivered to a patient in need thereof with a provisioning apparatus.

In any embodiment, a change in relative purity of a peptide in a therapeutic protein composition changes by about 10% or less after storage.

In any embodiment, a change in relative purity of a peptide in a therapeutic protein composition changes by about 5% or less after storage.

In any embodiment, a percent recovery of an initial mass of a peptide in a therapeutic protein composition after storage is at least about 80% of the initial mass of the peptide dissolved in a buffer forming the protein composition.

In any embodiment, at least about 80% or higher of an initial mass of a therapeutic peptide dissolved in a buffer composition is recoverable after storage.

In any embodiment, a peptide contains from about 20 to about 42 amino acid residue.

In any embodiment, the biological activity of a therapeutic protein composition does not change by more than about 10% after storage.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Figure 1:
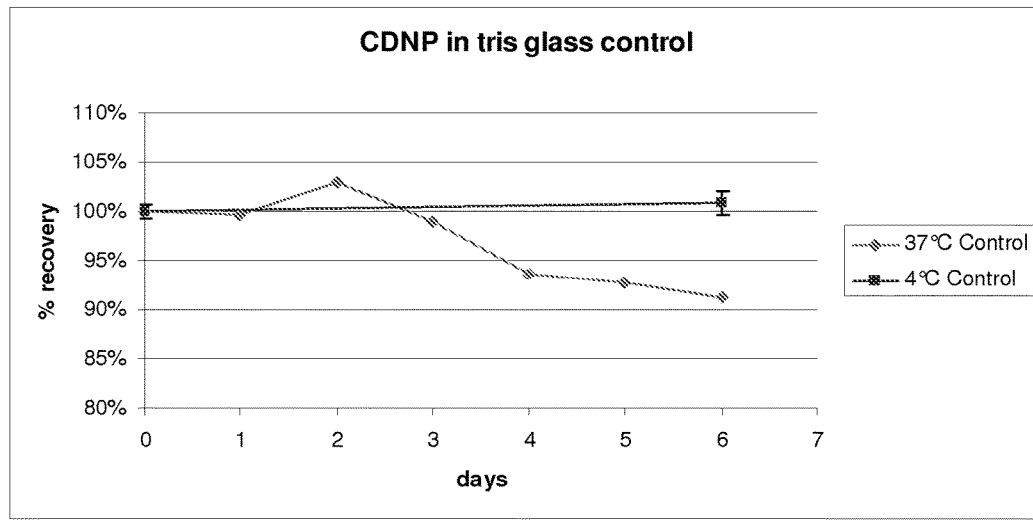
FIG. 1 shows the recovery of CD-NP stored as a 1 mg/mL solution in a tris-(hydroxymethyl)-aminomethane (Tris) buffer.

The delivery of chimeric natriuretic peptides stabilized in an aqueous solution is disclosed. The use of stabilized aqueous solutions of chimeric natriuretic peptides with a drug provisioning component are also disclosed that can include both programmable and constant rate subcutaneous infusion pumps, implanted, subcutaneous, or percutaneous vascular access ports, direct delivery catheter systems, local drug-release devices or any other type of medical device that can be adapted to deliver a therapeutic to a subject. The drug provisioning component can administer the chimeric natriuretic peptide subcutaneously, intramuscularly, or intravenously or direct to the kidney at a fixed, pulsed, continuous, or variable rate. In one embodiment of the invention contemplates subcutaneous delivery using an infusion pump at a continuous rate to maintain a specified plasma concentration of the chimeric natriuretic peptides.

DEFINITIONS

Unless defined otherwise, all technical and scientific terms used herein generally have the same meaning as commonly understood by one of ordinary skill in the relevant art. Generally, the nomenclature used herein for drug delivery, pharmacokinetics, pharmacodynamics, and peptide chemistry is well known and commonly employed in the art. Further, the techniques for the discussed procedures are generally performed according to conventional methods in the art.

The articles "a" and "an" are used herein to refer to one or to more than one (i.e., to at least one) of the grammatical object of the article. By way of example, "an element" means one element or more than one element.

The articles "a" and "an" are used herein to refer to one or to more than one (i.e., to at least one) of the grammatical object of the article. By way of example, "an element" means one element or more than one element.

The term "biological activity" refers to the ability of an agent or peptide to induce a specific physiological change in an organism or in a cell culture, such as an increase in the concentration or production of any cellular or biochemical component. In certain embodiments, "biological activity" refers to the ability of an agent or peptide to stimulate production of cGMP in a cell culture.

The term "comprising" includes, but is not limited to, whatever follows the word "comprising." Thus, use of the term indicates that the listed elements are required or mandatory but that other elements are optional and may or may not be present.

The term "consisting of" includes and is limited to whatever follows the phrase the phrase "consisting of." Thus, the phrase indicates that the limited elements are required or mandatory and that no other elements may be present.

The phrase "consisting essentially of" includes any elements listed after the phrase and is limited to other elements that do not interfere with or contribute to the activity or action specified in the disclosure for the listed elements. Thus, the phrase indicates that the listed elements are required or mandatory but that other elements are optional and may or may not be present, depending upon whether or not they affect the activity or action of the listed elements.

"Chronic Kidney Disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail to function at a sufficient level.

"Pharmaceutically acceptable" is meant to encompass any carrier, which does not interfere with effectiveness of the biological activity of the active ingredient and that is not toxic to the host to which it is administered.

"Drug provisioning component" or "drug provisioning apparatus" encompasses any and all devices that administers a therapeutic agent to a subject and includes infusion pumps, implanted, subcutaneous or percutaneous vascular access ports, direct delivery catheter systems, local drug-release devices, or any other type of medical device that can be adapted to deliver a therapeutic to a subject. The drug provisioning component and the control unit may be "co-located," which means that these two components, in combination, may make up one larger, unified unit of a system.

The term "initial composition," "initial therapeutic composition," "starting composition," or "starting therapeutic composition" refers to a composition having one or more active agents, such as a natriuretic peptide, that is newly constituted and has not been stored for a significant period of time.

"Glomerular filtration rate" describes the flow rate of filtered fluid through the kidney. The estimated glomerular filtration rate or "eGFR" is a measure of filtered fluid based on a creatinine test and calculating the eGFR based on the results of the creatinine test.

The term "inert gas" refers to any gas that one having ordinary skill in the art will recognize as not readily undergoing chemical reactions including oxidation reactions. Inert gases include nitrogen, helium, argon and noble gases.

A "patch pump" is a device that adheres to the skin, contains a medication, and can deliver the drug over a period of time, either transdermally, iontophoretically, or via an integrated or separate subcutaneous mini-catheter.

The term "delivering," "deliver," "administering," and "administers" can be used interchangeably to indicate the introduction of a therapeutic or diagnostic agent into the body of a subject in need thereof to treat a disease or condition, and can further mean the introduction of any agent into the body for any purpose.

The term "therapeutically effective amount" refers to an amount of an agent (e.g., chimeric natriuretic peptides) effective to treat at least one symptom of a disease or disorder in a subject. The "therapeutically effective amount" of the agent for administration may vary based upon the desired activity, the diseased state of the subject being treated, the dosage form, method of administration, subject factors such as the subject's sex, genotype, weight and age, the underlying causes of the condition or disease to be treated, the route of administration and bioavailability, the persistence of the administered agent in the body, evidence of natriuresis and/or diuresis, the type of formulation, and the potency of the agent.

The term "treating" and/or "treatment" refers to refer to the management and care of a subject having a pathology or condition by administration of one or more therapies and/or therapeutic compositions contemplated by the present invention. Treating also includes administering one or more methods or therapeutic compositions of the present invention or using any of the systems, devices or compositions of the present invention in the treatment of a subject. As used herein, "treatment" or "therapy" refers to both therapeutic treatment and prophylactic or preventative measures. "Treating" or "treatment" does not require complete alleviation of signs or symptoms, does not require a cure, and includes protocols having only a marginal or incomplete effect on a subject.

A "subject" or "patient" is a member of any animal species, preferably a mammalian species, optionally a human. The subject can be an apparently healthy individual, an individual suffering from a disease, or an individual being treated for a disease.

The term "sample" refers to a quantity of a biological substance that is to be tested for the presence or absence of one or more molecules.

"Absorption" refers to the transition of drug from the site of administration to the blood circulation.

"Adsorption" refers to the interaction of a substance with a surface where the substance adheres to the surface.

The "distal tip" of a catheter is the end that is situated farthest from a point of attachment or origin, and the end closest to the point of attachment or origin is known as the "proximal" end.

A "direct delivery catheter system," as used herein is a catheter system for guiding an elongated medical device into an internal bodily target site. The system can have a distal locator for locating a target site prior to deployment of the catheter. The catheter can be introduced through a small incision into the bodily vessel, channel, canal, or chamber in question; or into a bodily vessel, channel, canal, or chamber that is otherwise connected to the site of interest (or target site), and then guided through that vessel to the target site.

The terms "protein," "peptide," and "polypeptide" as used herein, describes an oligopeptide, polypeptide, or peptide polymer in which the monomers are amino acids that are joined together through amide bonds in at least part of the molecule. It will be understood by those of skill in the art that the peptides and recombinant peptides of the present invention can be made by varied methods of manufacture wherein the peptides of the invention are not limited to products of any of the specific exemplary processes listed herein.

The term "chimeric peptide(s)," as used herein is defined as artificial construct(s) consisting of bioactive compounds from at least two different peptides or two sequences from different parts of the same protein. Such multifunctional peptide combinations are prepared to enhance the biological activity or selectivity of their components. New biological effects can also be achieved with the chimera. In accordance with the present invention, the chimeric peptides are fusion peptide construct comprising different portions of any one of the natriuretic peptides.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. The present invention also provides for analogs of proteins or peptides which comprise a protein as identified above.

The term "fragment," as used herein, refers to a polypeptide that comprises at least six contiguous amino acids of a polypeptide from which the fragment is derived. In preferred embodiments, a fragment refers to a polypeptide that comprises at least 10 contiguous amino acids of a polypeptide from which the fragment is derived, more preferably at least 10 contiguous amino acids, still more preferably at least 15 contiguous amino acids, and still more preferably at least 20 contiguous amino acids of a polypeptide from which the fragment is derived.

As used herein, "cardiovascular disease" refers to various clinical diseases, disorders or conditions involving the heart, blood vessels, or circulation. Cardiovascular disease includes, but is not limited to, coronary artery disease, peripheral vascular disease, hypertension, myocardial infarction, and heart failure.

As used herein, "heart failure" (HF) refers to a condition in which the heart cannot pump blood efficiently to the rest of the body. Heart failure may be caused by damage to the heart or narrowing of the arteries due to infarction, cardiomyopathy, hypertension, coronary artery disease, valve disease, birth defects or infection. Heart failure may also be further described as chronic, congestive, acute, decompensated, systolic, or diastolic. The NYHA classification describes the severity of the disease based on functional capacity of the subject and is incorporated herein by reference.

Relating to heart failure, for example, "increased severity" of cardiovascular disease refers to the worsening of the disease as indicated by increased New York Heart Association (NYHA) classification, and "reduced severity" of cardiovascular disease refers to an improvement of the disease as indicated by reduced NYHA classification.

The "renal system," as defined herein, comprises all the organs involved in the formation and release of urine including the kidneys, ureters, bladder and urethra.

The term "phosphate buffer" refers to a buffer that contains monohydrogen phosphate ions ($HPO_4^{2-}$) and dihydrogen phosphate ions ($H_2PO_4^-$) regardless of the source from which such ions originate.

"Proteinuria" is a condition in which urine contains an abnormal amount of protein. One form of proteinuria is albuminuria, where the urine contains an abnormal amount of albumin protein. Albumin is the main protein in the blood. Healthy kidneys filter out waste products while retaining necessary proteins such as albumin. Most proteins are too large to pass through the glomeruli into the urine. However, proteins from the blood can leak into the urine when the glomeruli of the kidney are damaged. Hence, proteinuria is one indication of chronic kidney disease (CKD).

"Chronic kidney disease" (CKD) is a condition characterized by the slow loss of kidney function over time. The most common causes of CKD are high blood pressure, diabetes, heart disease, and diseases that cause inflammation in the kidneys. Chronic kidney disease can also be caused by infections or urinary blockages. If CKD progresses, it can lead to end-stage renal disease (ESRD), where the kidneys fail completely. In the Cardiorenal Syndrome (CRS) classification system, CRS Type I (Acute Cardiorenal Syndrome) is defined as an abrupt worsening of cardiac function leading to acute kidney injury; CRS Type II (Chronic Cardiorenal syndrome) is defined as chronic abnormalities in cardiac function (e.g., chronic congestive heart failure) causing progressive and permanent chronic kidney disease; CRS Type III (Acute Renocardiac Syndrome) is defined as an abrupt worsening of renal function (e.g., acute kidney ischaemia or glomerulonephritis) causing acute cardiac disorders (e.g., heart failure, arrhythmia, ischemia); CRS Type IV (Chronic Renocardiac syndrome) is defined as chronic kidney disease (e.g., chronic glomerular disease) contributing to decreased cardiac function, cardiac hypertrophy and/or increased risk of adverse cardiovascular events; and CRS Type V (Secondary Cardiorenal Syndrome) is defined as a systemic condition (e.g., diabetes mellitus, sepsis) causing both cardiac and renal dysfunction (Ronco et al., Cardiorenal syndrome, J. Am. Coll. Cardiol. 2008; 52: 1527-39). It is understood that CKD, as defined in the present invention, contemplates CKD regardless of the direction of the pathophysiological mechanisms causing CKD and includes CRS Type II and Type IV among others.

"Hemodynamics" is the study of blood flow or circulation. The factors influencing hemodynamics are complex and extensive but include cardiac output (CO), circulating fluid volume, respiration, vascular diameter and resistance, and blood viscosity. Each of these may in turn be influenced by physiological factors. Hemodynamics depends on measuring the blood flow at different points in the circulation. Blood pressure is the most common clinical measure of circulation and provides a peak systolic pressure and a diastolic pressure. "Blood pressure" (BP) is the pressure exerted by circulating blood upon the walls of blood vessels.

The term "intrinsic" is used herein to describe something that is situated within or belonging solely to the organ or body part on which it acts. Therefore, "intrinsic natriuretic peptide generation" refers to a subject's making or releasing of one or more chimeric natriuretic peptides by its respective organ(s).

"Cardiac output" (CO), or (Q), is the volume of blood pumped by the heart per minute (mL/min). Cardiac output is a function of heart rate and stroke volume. The heart rate is simply the number of heart beats per minute. The stroke volume is the volume of blood, in milliliters (mL), pumped out of the heart with each beat. Increasing either heart rate or stroke volume increases cardiac output. Cardiac Output in mL/min=heart rate (beats/min)×stroke volume (mL/beat).

A "buffer," "buffer composition" or "buffer solution" is an aqueous solution consisting of a mixture of a weak acid and its conjugate base or a weak base and its conjugate acid. A buffer solution can be formed by adding a weak acid to a solution wherein a portion of the weak acid spontaneously forms its conjugate base by hydrolysis or wherein the conjugate base forms by titration with a base. Similarly, a buffer solution can be formed by adding a weak base to a solution wherein a portion of the weak base spontaneously forms its conjugate acid by hydrolysis or wherein the conjugate acid forms by titration with an acid. A buffer solution may contain more than one species of a weak acid and its conjugate base or a weak base and its conjugate acid. Buffer solutions include solutions containing a weak acid or the conjugate acid of a weak base having a $pK_a$ from about 5 to about 8. A buffer solution can have a pH within about 1.5 units from the $pK_a$ of a weak acid or conjugate acid of a weak base present in the buffer solution. Some buffer solutions include solutions containing tris(hydroxymethyl) methylamine, monobasic phosphate, dibasic phosphate or phosphoric acid. A buffer solution does not require a specific concentration of a weak acid its conjugate base or a weak base and its conjugate acid.

The term "headspace" refers to the area of a container that is occupied by gas and not occupied by a liquid.

The term "peptide chain" refers to the part of a molecule formed from a region of peptide bonds between amino acid resides, where the peptide chain can be covalently linked to another peptide chain through the side-chains of the amino acid residues, such as a disulfide bridge.

The term "recovery" in relation to the presence of proteins, peptides or polypeptides in a solution or composition refers to an amount of the total mass of proteins, peptides or polypeptides present in a measured sample at a beginning of a time period or the absorption of light at an appropriate wavelength by proteins, peptides or polypeptides present in a measured sample at a beginning of a time period in relation to the total mass or light absorption of proteins, peptides or polypeptides present in the same solution or composition after the elapse of the time period.

The term "percent recovery" refers to the mass of proteins, peptides or polypeptides in a measured sample or the absorption of light at an appropriate wavelength by protein, peptides or polypeptides in a measured sample expressed as a percent relative to the mass or light absorption of proteins, peptides or polypeptides in an initial or starting sample before exposure of the solution to elevated temperature or mechanical stress.

The term "purity" refers to percentage of mass of a protein, peptide or polypeptide in a solution that has the same chemical identity. Chemical identity can be determined by suitable analytical techniques such as high performance liquid chromatography and reverse-phase high performance liquid chromatography.

The term "change in relative purity" refers to a normalized change in purity, as measured as a percentage, for a protein, peptide or polypeptide from an initial purity to a purity measured at a later time.

The terms "natriuretic" or "natriuresis" refer to the ability of a substance to increase sodium clearance from a subject.

The terms "renal protective" and "reno-protective" refer to the ability of a substance to improve one or more functions of the kidneys of a subject, including natriuresis, diuresis, cardiac output, hemodynamics or glomerular filtration rate, or to lower the blood pressure of the subject.

The term "stability" refers to the degree of recovery or purity of a protein, peptide or polypeptide from a solution and/or the maintenance of the purity of the protein, peptide or polypeptide in solution, or any measure of biological activity.

The term "at a temperature" or any reference to maintain any mixture, solution or composition refer to the maintenance of the mixture, solution or composition at the specified temperature for at least a majority of a referenced time period, where the mixture, solution or composition can be at a different temperature for a portion of the time period.

The term "therapeutic composition" refers to a composition having an amount of a natriuretic peptide, in a chimeric natriuretic peptide as described herein.

Natriuretic Peptides and Chimeric Natriuretic Peptides

The natriuretic peptides have been the focus of intense study subsequent to the seminal work by DeBold et al. on the potent diuretic and natriuretic properties of atrial extracts and its precursors in atrial tissues (A rapid and potent natriuretic response to intravenous injection of atrial myocardial extract in rats, Life Sci., 1981; 28(1): 89-94). Some natriuretic peptides are a family of peptides having a 17 amino acid disulfide ring structure acting in the body to oppose the activity of the renin-angiotensin system. That is, a natriuretic peptide may have an intramolecular disulfide bond between two cysteine residues in the same peptide chain, wherein 15 ammo acid residues in the peptide chain are located between the two cysteine residues forming the disulfide. In humans, the family consists of atrial natriuretic peptide (ANP), brain natriuretic peptide (BNP) of myocardial cell origin, C-type natriuretic peptide (CNP) of endothelial origin, and urodilatin (URO), which is thought to be derived from the kidney. Atrial natriuretic peptide (ANP), alternatively referred to in the art as Atrial natriuretic factor (ANF), is secreted by atrial myocytes in response to increased intravascular volume. Once ANP is in the circulation, its effects are primarily on the kidney, vascular tissue, and adrenal gland. ANP leads to the excretion of sodium and water by the kidneys and to a decrease in intravascular volume and blood pressure. Brain natriuretic peptide (BNP) also originates from myocardial cells and circulates in human plasma similar to ANP. BNP is natriuretic, renin inhibiting, vasodilating, and lusitropic. C-type natriuretic peptide (CNP) is of endothelial cell origin and functions as a vasodilating and growth-inhibiting polypeptide. Natriuretic peptides have also been isolated from a range of other vertebrates. For example, *Dendroaspis angusticeps* natriuretic peptide is detected in the venom of *Dendroaspis angusticeps* (the green mamba); CNP analogues are cloned from the venom glands of snakes of the Crotalinae subfamily; *Pseudocerastes persicus* natriuretic peptide is isolated from the venom of the Iranian snake (*Pseudocerastes persicus*), and three natriuretic-like peptides (TNP-a, TNP-b, and TNP-c) are isolated from the venom of the Inland Taipan (Oxyuranus microlepidotus). Because of the capacity of natriuretic peptides to restare hemodynamic balance and fluid homeostasis, they can be used to manage cardiopulmonary and renal symptoms of cardiac disease due to its vasodilator, natriuretic and diuretic properties.

Within the 126 amino acid (a.a.) ANP prohormone are four peptide hormones: long acting natriuretic peptide (LANP) (also known as proANP 1-30) (a.a. 1-30), vessel dilator (VD) (a.a. 31-67), kaliuretic peptide (KP) (a.a. 79-89), and atrial natriuretic peptide (ANP) (a.a. 99-126), whose main known biologic properties are blood pressure regulation and maintenance of plasma volume in animals and humans.

The fifth member of the atrial natriuretic peptide family, urodilatin (URO) (ANP a.a. 95-126) is isolated from human urine and has an N-terminal extension of four additional amino acids, as compared with the circulating form of ANP (a.a. 99-126). This hormone is synthesized in the kidney and exerts potent paracrine renal effects. (Meyer, M. et al., Urinary and plasma urodilatin measured by a direct RIA using a highly specific antiserum, Clin. Chem., 1998; 44(12):2524-2529). Several studies have suggested that URO is involved in the physiological regulation of renal function, particularly in the control of renal sodium and water excretion wherein a concomitant increase in sodium and URO excretion was observed after acute volume load and after dilation of the left atrium. Additionally, infusions and bolus injections of URO in rats and healthy volunteers have also revealed the pharmacological potency of this natriuretic peptide wherein intense diuresis and natriuresis as well as a slight reduction in blood pressure are the most prominent effects. The strength and duration of these effects differ considerably from ANP a.a. 99-126.

Recently, two chimeric natriuretic peptides have been synthesized and are undergoing clinical study. The first of these is CD-NP (SEQ ID No. 1), which comprises the 22 amino acid human C-type natriuretic peptide (CNP), described as (SEQ ID No. 2), and the 15 amino acid C-terminus of Dendroaspis natriuretic peptide (DNP) (SEQ ID No. 3) as described in U.S. Pat. No. 7,754,852, the contents of which are incorporated in their entirety by reference. CD-NP is designed to enhance the renal actions of CNP, which is a ligand for natriuretic peptide receptor B (NPR-B), without inducing excessive hypotension.

```
CNP
                                         (SEQ ID No. 2)
GLSKGCFGLKLDRIGSMSGLGC

CD-NP
                                         (SEQ ID No. 1)
GLSKGCFGLKLDRIGSMSGLGCPSLRDPRPNAPSTSA

DNP (C-terminus)
                                         (SEQ ID No. 3)
PSLRDPRPNAPSTSA
```

Similarly, the chimeric natriuretic peptide CU-NP (SEQ ID No. 4) is designed to preserve the favorable actions of urodilatin (URO), which is a natriuretic peptide receptor A (NPR-A) agonist, while also minimizing hypotension. CU-NP consists of the 17 amino acid ring of human CNP (SEQ ID No. 5) and the N- and C-termini of urodilatin (SEQ ID Nos. 6-7, respectively). The first ten amino acid residues of CU-NP (SEQ ID No. 4) correspond to amino acid residues 1 to 10 of urodilatin (SEQ ID No. 6). Amino acid residues 11 to 27 of CU-NP correspond to amino acid residues 6 to 22 of human mature CNP (SEQ ID No. 5). Amino acid residues 28 to 32 of CU-NP correspond to amino acid residues 26 to 30 of Urodilatin (SEQ ID No. 7).

```
CU-NP
                                           (SEQ ID No. 4)
TAPRSLRRSSCFGLKLDRIGSMSGLGCNSFRY (SEQ ID No. 5)
CFGLKLDRIGSMSGLGC (SEQ ID No. 6)
TAPRSLRRSS (SEQ ID No. 7)
NSFRY
```

Of the 20 ammo acids commonly forming peptides and proteins, valine, isoleucine, leucine, methionine, proline, phenylalanine, and tryptophan are particularly hydrophobic. In certain embodiments, a protein, peptide or polypeptide contained in a therapeutic composition has about 30% of the amino acid resides therein selected from valine, isoleucine, leucine, methionine, proline, phenylalanine, and tryptophan. In certain other embodiments, a protein, peptide or polypeptide contained in a therapeutic composition has about 32% of the amino acid resides therein selected from valine, isoleucine, leucine, methionine, proline, phenylalanine, and tryptophan. In certain embodiments, the protein, peptide or polypeptide in the therapeutic protein composition has from about 20 to about 40 amino acid residues.

Both CD-NP and CU-NP can be synthesized using solid phase methods on an ABI 431A Peptide Synthesizer (PE Biosystems, Foster City, Calif.) on a pre-loaded Wang resin with N-Fmoc-L-amino acids (SynPep, Dublin, Calif.). The synthesized peptide can then be confirmed using high-performance liquid chromatography or mass spectrometry, such as by electrospray ionization mass analysis on a Perkin/Elmer Sciex API 165 Mass Spectrometer (PE Biosystems). An example of the method of synthesis of CD-NP is as described by Lisy et al. (Design, Synthesis, and Actions of a Novel Chimeric Natriuretic Peptide: CD-NP, J. Am. Coll. Cardiol., 2008; 52:60-68), which is incorporated by reference in its entirety.

Studies have established the beneficial vascular and antiproliferative properties of C-type natriuretic peptide (CNP). Without being limited to any theory, although it lacks renal actions, CNP is believed to be less hypotensive than the cardiac peptides atrial natriuretic peptide (ANP) and B-type natriuretic peptide (BNP) and instead is thought to unload the heart due to venodilation. This feature may be due to the ability of CNP to activate NPR-B receptors in veins only, whereas ANP and BNP bind to NPR-A receptors in both arteries and veins. (Lisy et al., 2008) Dendroaspis natriuretic peptide (DNP) is a potent natriuretic and diuretic peptide that is markedly hypotensive and functions via a separate receptor linked to guanylyl cyclase than CNP. Thus, CD-NP has the following effects in vivo: it is natriuretic and diuretic, glomerular filtration rate enhancing, cardiac unloading, and renin inhibiting. CD-NP also demonstrates less hypotensive properties when compared with BNP. In addition, CD-NP activates cyclic guanosine monophosphate and inhibits cardiac fibroblast proliferation in vitro. CD-NP is also designed to resist degradation. Without being limited to any theory, the long C-terminus of DNP may be resistant to degradation by neutral endopeptidase (NEP), and the lack of CNP may explain its increased susceptibility to NEP degradation when delivered alone. Thus, CD-NP was synthesized with the goal of combining the above complementary profiles of CNP and DNP into a single chimeric peptide.

Additional natriuretic peptides are known that share sequence homology with CD-NP peptide (SEQ ID No. 1). These additional natriuretic peptides vary in their ability to serve as activators of NPR-A and NPR-B relative to CD-NP peptide. CD-NP peptide has the ability to activate NPR-A and NPR-B; however, CD-NP peptide possibly acts as only a partial agonist to NPR-A and NPR-B where other peptides are able to induce higher guanylyl cyclase activity in NPR-A and/or NPR-B at saturating concentrations. A variant of CD-NP is a peptide having the sequence GLSKGCFGRKMDRIGSMSGLGCPSLRDPRPNAPSTSA (SEQ ID No. 8), which differs in amino acid residues 9-11 compared with CD-NP peptide (SEQ ID No. 1) and has the two cysteine residues involved in a disulfide bond. SEQ ID No. 8, which can be referred to as B-CDNP, has a higher affinity for binding NPR-A and produces higher guanylyl cyclase activity in NPR-A compared with CD-NP peptide. B-CDNP peptide retains the ability to activate NPR-B as well.

An additional variant of CD-NP is a peptide having the sequence GLSKGCFGLKLDRISSSSGLGCPSLRDPRPNAPSTSA (SEQ ID No. 9), which differs in amino acid residues 15-17 compared with CD-NP peptide (SEQ ID No. 1) and has the two cysteine residues involved in a disulfide bond. SEQ ID No. 9, which can be referred to as CDNP-B, has the ability to act as a full agonist for NPR-A in a manner similar to BNP while maintain an ability to activate NPR-B as well.

Natriuretic peptides as defined herein expressly include variants of CD-NP (SEQ ID No. 3), B-CDNP (SEQ ID No. 8) and CDNP-B (SEQ ID No. 9) having an ability to activate NPR-A and/or NPR-B, where no more than 1, no more than 2, no more than 3, no more than 4, or no more than 5 amino acid residues of the sequences are added, deleted or substituted. Variants include peptides where there is a combination of additions, deletions or substitutions. Substitution of amino acid residues refers to the replacement of any amino acid residue of SEQ ID No.'s 1, 8 and 9 with any other amino acid residue. Further, amino acid substitutions can be conservative amino acid substitutions. Conservative amino acid substitutions are substitutions where an amino acid residue is replaced with another amino acid residue having similar, size, charge, hydrophobicity and/or chemical functionality. Non-limiting examples of conservative amino acid substitutions include, but are not limited to, replacing an amino acid residue appearing in one of the following groups with another amino acid residue from the same group: 1) aspartic acid and glutamic acid as acidic amino acids; 2) lysine, arginine, and histidine as basic amino acids; 3) leucine, isoleucine, methionine, valine and alanine as hydrophobic amino acids; 4) serine, glycine, alanine and threonine as hydrophilic amino acids; 5) glycine, alanine, valine, leucine, isoleucine as aliphatic group residues; 6) a group of amino acids having aliphatic-hydroxyl side chains including serine and threonine; 7) a group of amino acids having amide-containing side chains including asparagine and glutamine; 8) a group of amino acids having aromatic side chains including phenylalanine, tyrosine, and tryptophan; 9) a group of amino acids having basic side chains including lysine, arginine, and histidine; and 10) a group of amino acids having sulfur-containing side chains including cysteine and methionine. The ability of variants to activate NPR-A or NPR-B can be assessed using the assays described in International Patent Publication WO 2010/048308 (PCT/US2009/061511), which is incorporated herein by reference. In certain embodiments, a variant of CD-NP (SEQ ID No. 1), B-CDNP (SEQ ID No. 8) or CDNP-B (SEQ ID No. 9) has less than about 42 amino acid residues.

Variants of B-CDNP peptide expressly includes variants having the sequence GLSKGCFGX 1X 1X2DRIGSMSGLGCPSLRDPRPNAPSTSA (SEQ ID No. 10) and variants of CDNP-B peptide include GLSKGCF-GLKLDRIX 3X3X3SGLGCPSLRDPRPNAPSTSA (SEQ ID No. 11), wherein $X_1$ is selected from the group consisting of lysine, arginine, and histidine, $X_2$ is selected from the group consisting of leucine, isoleucine, methionine, valine and alanine, and $X_3$ is selected from the group consisting of serine, glycine, alanine and threonine.

One obstacle to delivering peptides in a clinically effective manner is that peptides generally have poor delivery properties due to the presence of endogenous proteolytic enzymes, which are able to quickly metabolize many peptides at most mutes of administration. Further, peptides may decompose and/or absorb on the surface of a container during storage or onto the surfaces of the conduits, IV lines, and pumps used to deliver peptides either by bolus or infusion to a subject via an intravenous or subcutaneous (SQ) administration route. Such complications are amplified for therapeutic protein compositions formulated for delivery by a continuous infusion device or pump, where the therapeutic protein composition will experience elevated temperatures and mechanical stress.

Stability of Therapeutic Protein Compositions

The therapeutic proteins, peptides or polypeptides, including CD-NP and variants thereof described above, have high stability in buffers containing tris-(hydroxymethyl)-aminomethane ("Tris") or phosphate buffer. Aqueous compositions of therapeutic proteins or peptides are typically formulated several weeks, if not months, prior to actual use for administration to a subject. Further, the stability of a therapeutic protein composition can be affected based upon the type of container holding the therapeutic protein composition. For example, a therapeutic protein can be distributed to commercial pharmacies in a glass container. However, when used in a pump or infusion device, the therapeutic protein composition can come into contact with plastic or metal surfaces that may affect the stability of any proteins, peptides or polypeptides contained in the therapeutic composition.

During use of the therapeutic composition in an infusion device or pump, the composition can be exposed to elevated temperatures in addition to mechanical stress. Elevated temperature is the result of both the location of the pump near the body heat of the subject and due to the mechanical action of the pump. Further, it is desirable to inject a therapeutic composition that is not too different from the body temperature of an individual. The therapeutic protein compositions disclosed herein have enhanced stability in the temperature range from about 25 to about 45° C. and any range in between. The therapeutic protein compositions also have enhanced stability at room temperatures of about 20 to about 30° C. and any range in between. For long term storage, the therapeutic protein compositions described herein are stable for storage at refrigerated temperatures from about 4 to about 15° C. and any range in between.

It is desirable for formulations of therapeutic agents, including formulations of synthetic peptides, to be stable over time. Stability is the tendency of the chemical composition and physical properties of the therapeutic formulation to remain unchanged over time. Stable formulations are indicated by a consistent recovery of peptide or protein mass from solution, which is an indication of a lack of surface adsorption of the peptide and/or a lack of aggregation of the peptide that results in precipitation. Stable formulations are also indicated by a lack of chemical change to the one or more peptides or proteins in the therapeutic composition. Peptides, particularly peptides synthesized by solid phase methods, are discrete molecular species having uniform molecular weight with the exception of ionizable groups. Chemical modifications to a peptide include hydrolysis of the peptide backbone to form two or more peptides and/or modifications to side-chains such as oxidation, esterification, etc. Chemical modifications to a peptide do not necessarily cause the removal of mass from the aqueous formulation. However, chemical modifications to a peptide affect the stability of therapeutic formulations since the peptide species having pharmaceutical properties is degraded by the degree of chemical change.

A stable therapeutic composition has a near constant peptide content or recovery over time and exhibits consistency in the molecular species or purity observed to be present in the composition. For example, a therapeutic composition formulated with one molecular peptide species will contain substantially only that particularly molecular peptide species over time. Likewise, a therapeutic composition formulated with two molecular peptide species will contain substantially only those two species in the same proportion over time. It should be noted that the observation of a high degree of recovery from a therapeutic composition or purity of molecular species in a therapeutic composition is an indication of overall stability.

In any embodiment, at least about 80% of the mass of one or more peptides contained in a therapeutic composition are recoverable and still distributed in the composition after storage for a period of at least 6 days and the purity of such recovered peptides is at least about 80%. In certain other embodiments, at least about 85% of the mass of one or more peptides contained in a therapeutic composition are recoverable and still distributed in the composition after storage for a period of at least 6 days and the purity of such recovered peptides is at least about 85%. In certain additional embodiments, at least about 90% of the mass of one or more peptides contained in a therapeutic composition are recoverable and still distributed in the composition after storage for a period of at least 6 days and the purity of such recovered peptides is at least about 90%. In still further embodiments, at least about 95% of the mass of one or more peptides contained in a therapeutic composition are recoverable and still distributed in the composition after storage for a period of at least 6 days and the purity of such recovered peptides is at least about 95%. In yet further embodiments, at least about 97% of the mass of one or more peptides contained in a therapeutic composition are recoverable and still distributed in the composition after storage for a period of at least 6 days and the purity of such recovered peptides is at least about 97%.

The therapeutic protein compositions described herein have a pH from about 6.5 to about 7.6 and any range in between. The therapeutic protein composition can have a pH from about 6.5 to 7.6 at any temperature or have a composition such that the pH is from about 6.5 to 7.6 when the therapeutic protein composition is adjusted to a temperature of 25° C.

In any embodiment, the therapeutic protein composition contains additional components. Examples of additional components include meta-cresol (m-cresol) and glycerol. In certain embodiments, the concentration of m-cresol in the therapeutic protein composition is from about 0.15 to about 0.315% by weight, including all possible sub-ranges, such as from 0.15-0.2%, from 0.15-0.25%, from 0.15-0.3%, from 0.15-0.31%, from 0.2-0.25%, from 0.2-0.3%, from 0.2-0.31%, from 0.2-0.315%, from 0.215%-0.23%, from 0.215%-0.235%, from 0.215%-0.27%, from 0.215%-0.3%, from 0.215%-0.315%, from 0.23%-0.24%, from 0.23%-0.245%, from 0.23%-0.25%, from 0.23%-0.26%, from 0.23%-0.27%, etc. In certain embodiments, the concentration of glycerol in the therapeutic protein composition ranges from greater than 0 to about 5%, as represented by the range from n to (n+i), where n={x E lffi.IO<x 5} and i={y E lffi.IO y (5−n)}. In certain other embodiments, the concentration of glycerol in the therapeutic protein composition is from about 0.1 to about 5% by weight.

In any embodiment, the concentration of Tris buffer in the therapeutic protein composition is from about 5 to about 200 mM including all possible sub-ranges, for example from about 5 to about 100 mM, from about 10 to about 190 mM, from about 25 to about 175 mM, from about 35 to about 170 mM, from about 45 to about 150 mM, from about 50 to about 125 mM, from about 75 to about 110 mM, from about 85 to about 100 mM, from about 95 to about 180 mM, from about 125 to about 170 mM, from about 85 to about 110 mM, from about 95 to about 105 mM, from about 5 to about 85 mM, from about 15 to about 75 mM, from about 25 to about 50 mM or from about 10 to about 70 mM.

In any embodiment, the concentration of phosphate buffer (dihydrogen phosphate salts and monohydrogen phosphate salts, combined) in the therapeutic protein composition is from about 0.2 to about 10 grams per liter including all possible sub-ranges. For example, the concentration of phosphate buffer in the therapeutic protein composition is from about 0.5 to about 5 grams per liter or from about 1 to about 4 grams per liter. In any embodiment, the concentration of sodium chloride in the therapeutic protein composition is from about 2 to about 15 grams per liter. In any embodiment, the concentration of sodium chloride in the therapeutic protein composition is from about 5 to about 10 grams per liter. In further embodiments, the therapeutic protein composition contains a physiological amount of sodium chloride.

In any embodiment, the therapeutic protein compositions have a concentration of one or more proteins, polypeptides or peptides that is higher than the concentration in a composition for direct administration to a subject. The therapeutic protein composition can serve as a concentrated stock solution appropriate for storage that is diluted to a working concentration prior to administration to a subject. In any embodiment, the therapeutic protein composition has a concentration of one or more proteins, polypeptides and peptides from about 0.05 to about 20 mg/mL including all possible sub-ranges, such as from about 0.10 to about 15 mg/mL, 0.05 to about 10 mg/mL, 0.10 to about 7 mg/mL, 0.10 to about 5 mg/mL, 3 to about 7 mg/mL, 4 to about 8 mg/mL, 2 to about 4 mg/mL, 3 to about 9 mg/mL, 6 to about 10 mg/mL, or from about 0.05 to about 8 mg/mL. In any embodiment, the therapeutic protein composition can be diluted by a factor from about 10 to about 100 prior to administration to a subject.

One obstacle to delivering peptides in a clinically effective manner is that peptides can decompose and/or absorb on the surface of a container during storage or onto the surfaces of the conduits, IV lines, and pumps used to deliver peptides either by bolus or infusion to a subject via an intravenous or subcutaneous (SQ) administration route. Such complications are amplified for therapeutic protein compositions formulated for delivery by a continuous infusion device or pump, where the therapeutic protein composition will experience mechanical stress.

In any embodiment, a therapeutic composition remains stable during administration from a provisioning apparatus over an extended period of time, for example after a 6-day period of time. In any embodiment, the recovery of a natriuretic peptide from a composition stored and administered from a provisioning apparatus is about 90% or more when the provisioning apparatus is operated at a temperature from about 25 to about 45° C. for a period of at least about 6 days. In any embodiment, the recovery of a natriuretic peptide from a composition stored and administered from a provisioning apparatus is about 92% or more when the provisioning apparatus is operated at a temperature from about 25 to about 45° C. for a period of at least about 6 days. In any embodiment, the recovery of a natriuretic peptide from a composition stored and administered from a provisioning apparatus is about 93% or more when the provisioning apparatus is operated at a temperature from about 25 to about 45° C. for a period of at least about 6 days. Recovery is measured relative to a starting or initial composition containing the natriuretic peptide.

In any embodiment, the recovery of a natriuretic peptide from a composition stored and administered from a provisioning apparatus is about 80% or more when the provisioning apparatus is operated at a temperature from about 25 to about 45° C. for a period of at least about 6 days. In certain further embodiments, the recovery of a natriuretic peptide from a composition stored and administered from a provisioning apparatus is about 85% or more when the provisioning apparatus is operated at a temperature from about 25 to about 45° C. for a period of at least about 6 days.

Those skilled in the art will readily understand that methods for synthesizing artificial peptides may not be capable of producing a peptide product having 100% purity. That is, a peptide produced by a method such as solid phase synthesis will contain impurities undermost conditions such that a composition formed from the synthesized peptide will have a purity less than 100%. Peptides produced by recombinant methods will also have purities less than 100% in most instances. An initial formulation a composition containing a peptide will have a starting purity of less than 100%. A change in relative purity of the peptide can be measured from the initial purity of the peptide over a period of time. The initial purity of a peptide is the purity of the peptide as synthesized or otherwise obtained and a measured purity is the purity of a composition containing the peptide after a period of time. The change in relative purity can be calculated using the following equation:

$$\text{Change in Relative Purity} = \frac{\text{Initial Purity} - \text{Measured Purity}}{\text{Initial Purity}}$$

For example, if a peptide has an initial purity of 98% and a measured purity in a composition of 95% after 1 week, then the change in purity is 3% while the change in relative purity is 3.06%.

It will be apparent to one skilled in the art that various combinations and/or modifications and variations can be made, and that features illustrated or described as being part of one embodiment may be used on another embodiment to yield a still further embodiment.

Example 1

Preparation of Tris Buffer with 0.25% (Wt.) Meta-Cresol 16.0 g glycerol, 6.05 g tris-(hydroxymethyl)-aminomethane ("Tris"), 2.50 g meta-cresol were mixed in a 1.00 L volumetric flask. Approximately 900 mL nanopure water was added to the volumetric flask and the mixture was magnetically stirred to reach complete dissolution. 4 normal hydrochloric acid was used to adjust pH to 7.3 at 25° C. Then, the flask was filled to 1 L mark with nanopure water. The pH was rechecked and verified to be 7.3 at 25° C. The pH 7.3 Tris buffer was stored at 2-8° C. until use.

In any embodiment, the Tris buffer is degassed by purging with nitrogen or other inert gas prior to use. Further, the Tris buffer can be stored in container where any headspace in the container has been purged with nitrogen or another inert gas.

Tris and glycerol were acquired from Sigma-Aldrich (St. Louis). Meta-cresol was obtained from Harrell Industries.

Example 2

Preparation of Phosphate Buffered Saline (PBS) with 0.25% (Wt.) Meta-Cresol 7.50 g Sodium Chloride, 1.80 g sodium dihydrogenphosphate, 1.30 g sodium monohydrogenphosphate and 2.5 g meta-cresol were mixed in 1.00 L volumetric flask. After adding approximately 900 mL nanopure water, the mixture was magnetically stirred to reach complete dissolution. One normal aqueous sodium hydroxide solution was titrated to adjust pH to 7.4 at 25° C. Then, the flask was filled to 1 L mark with nanopure water. The pH was rechecked and verified to be 7.4 at 25° C. The pH 7.4 PBS was store at 2-8° C. until use.

In any embodiment, the PBS is degassed by purging with nitrogen or other inert gas prior to use. Further, the PBS can be stored in container where any headspace in the container has been purged with nitrogen or another inert gas.

Sodium chloride, sodium dihydrogenphosphate, and sodium monohydrogenphosphate were acquired from Sigma-Aldrich (St. Louis). Meta-cresol was obtained from Harrell Industries.

Example 3

Preparation of Compositions Containing CD-NP

Stock solution compositions of CD-NP were prepared in both the Tris buffer described in Example 1 and the PBS described in Example 2. Stock solution compositions were prepared at a concentration of 1 mg/mL of CD-NP. 2 mg of CD-NP were placed in a glass vial with a septa cap. 2 mL of the Tris buffer of Example 1 or 2 mL of the PBS of Example 2 was added by a needle through the septa cap and mixed well by gentle inversion. Larger volumes of solution were prepared by combining the solutions formed from individual 2 mg vials of CD-NP.

To improve stability, the headspace of any container containing or storing a composition containing a natriuretic peptide can be flushed with nitrogen or another inert gas. Further, the reservoir of any provisioning apparatus can similarly be flushed with nitrogen or an inert gas.

Example 4

Stability of 1 mg/mL CD-NP Tris Buffer Solution Stored in Glass

The stability of CD-NP in solution at 4° C. and 37° C. was assessed using high-performance liquid chromatography (HPLC). Percent recovery was calculated for the 4° C. glass vial control samples by dividing the peak area (mAU) of the CD-NP peak observed during Strong-Cation Exchange (SCX)-HPLC after storage of a sample for a period of time by the peak area observed shortly after dissolving CD-NP in the appropriate buffer. Percent recovery was calculated for the 37° C. glass vial control samples, the pumped samples and the pump residual samples, as described below, by dividing the peak area (mAU) of the CD-NP peak after storage of a sample for a period of time by the peak area (mAU) observed in the control samples stored at 4° C. for 6 days. Purity was calculated by dividing the peak area of the peak representing CD-NP observed during HPLC by the total chromatographic peak area observed during HPLC.

Eleven glass vials were prepared containing the CD-NP stock formulation by adding 200 µL of CD-NP stock formulation to 1.6 mL HPLC vials. Five vials were stored at 4° C. with no agitation for use as control references. The remaining 6 vials were stored at 37° C. without agitation. The 5 vials stored at 4° C. were analyzed by Strong-Cation Exchange (SCX)-HPLC shortly after reconstitution of the CD-NP (Day 0) and after a 6-day period. One of the 6 vials stored at 37° C. was transferred to 4° C. at each time point (Days 1, 2, 3, 4, 5 and 6). All 37° C. samples were assayed in a single SCX-HPLC assay, along with the 4° C. control samples on Day 6. The SCX-HPLC analysis procedure is described in Table 1 below, where the same analysis procedure for SCX-HPLC was used for all Examples described herein.

TABLE 1

| Strong-Cation Exchange (SCX)-HPLC method | |
|---|---|
| Parameter | Description |
| HPLC instrument | Waters 2695 with 2998 PDA Detector |
| Column | PolyLC PolySULFOETHYL A, 2000 × 4.6 mm, 5 µm, 300 Å, P/N 204SE0503 |
| Software | Waters Empower 2 |
| Mobile Phase A (MPA) | 5 mM $KH_2PO_4$ & 5 mM $NaClO_4$ in $H_2O$:ACN (60:40) Adjusted to pH 4.0 |
| Mobile Phase B (MPB) | 5 mM $KH_2PO_4$ & 252 mM $NaClO_4$ in $H_2O$:ACN (60:40) Adjusted to pH 4.0 |
| Flow Rate | 0.8 mL/min |
| Detection Wavelength | 215 nm |
| Column Temperature | 45° C. |
| Autosampler Temperature | 5° C. |
| Run Time | 47 Minutes |
| Injection Volume | 20 µL |

TABLE 1-continued

Strong-Cation Exchange (SCX)-HPLC method

| Parameter | Description | | |
|---|---|---|---|
| HPLC Gradient: | Time (minutes) | % MPA | % MPB |
| | 0.0 | 75 | 25 |
| | 10 | 45 | 55 |
| | 26 | 45 | 55 |
| | 34 | 0 | 100 |
| | 39 | 0 | 100 |
| | 39.01 | 75 | 25 |
| | 47 | 75 | 25 |

The results for a recovery determination for 1 mg/mL CD-NP dissolved in the Tris buffer of Example 1 are presented in Table 2 and provided in graphical form in FIG. 1. Recovery was calculated as a percentage of the average peak area (mAU) of the 4° C. reference samples. The recovery of CD-NP from the 1 mg/mL solution was measured for the samples stored at 37° C. for 1, 2, 3, 4, 5 and 6 days and after 6 days of storage for the reference samples stored at 4° C. As shown in Table 2 and FIG. 1, the recovery of CD-NP remained stable after 6 days of storage at 4° C. The recovery of CD-NP decreased over a 6 day period of storage at 37° C., although the recovery remained stable during the first 3 days of storage. After a 6 day period of storage at 37° C., the recovery of CD-NP peptide remained greater than about 90%. After a 5 day period of storage at 37° C., the recovery of CD-NP remained greater than about 92%.

In certain embodiments, a therapeutic protein composition stored at a temperature from about 25 to about 45° C. for a period of 6 days has a recovery of a protein, peptide or polypeptide at least about 90% compared to the beginning of the 6 day period. In certain other embodiments, a therapeutic protein composition stored at a temperature from about 25 to about 45° C. for a period of 5 days has a recovery of a protein, peptide or polypeptide of at least about 92%. In certain other embodiments, a therapeutic protein composition stored at a temperature from about 25 to about 45° C. for a period of 3 days has a recovery of a protein, peptide or polypeptide of at least about 98%.

TABLE 2

Recovery of CD-NP in Tris buffer solution from glass vials

| Day | 4° C. % Recovery vs. average Day 0 peak area Ave ± SD (n = 5) | 37° C. % Recovery vs. Day 6 4° C. Controls |
|---|---|---|
| 0 | 100.0% ± 1.7% | 100.0% |
| 1 | n/a | 99.7% |
| 2 | n/a | 103.0% |
| 3 | n/a | 99.0% |
| 4 | n/a | 93.7% |
| 5 | n/a | 92.8% |
| 6 | 98.5% ± 0.7% | 91.2% |

Table 3 presents the results of purity determinations for 1 mg/mL CD-NP dissolved in the Tris buffer of Example 1. As shown in Table 3, the purity of CD-NP remained stable after 6 days of storage at 4° C. The purity of the same solution stored at 37° C. decreased in purity over a 6 day time period. After a 6 day period of storage at 37° C., the purity of CD-NP remained greater than about 90%.

TABLE 3

Purity of CD-NP in Tris buffer solution from glass vials

| Day | 4° C. Glass Vial Ave ± SD, n = 5 | 37° C. Glass Vial |
|---|---|---|
| 0 | 96.76% ± 0.01 | |
| 1 | n/a | 96.12% |
| 2 | n/a | 95.41% |
| 3 | n/a | 94.92% |
| 4 | n/a | 93.34% |
| 5 | n/a | 92.92% |
| 6 | 96.62% ± 0.14% | 91.32% |

Example 5

Stability of 1 mg/mL CD-NP PBS Solution Stored in Glass

Figure 2:
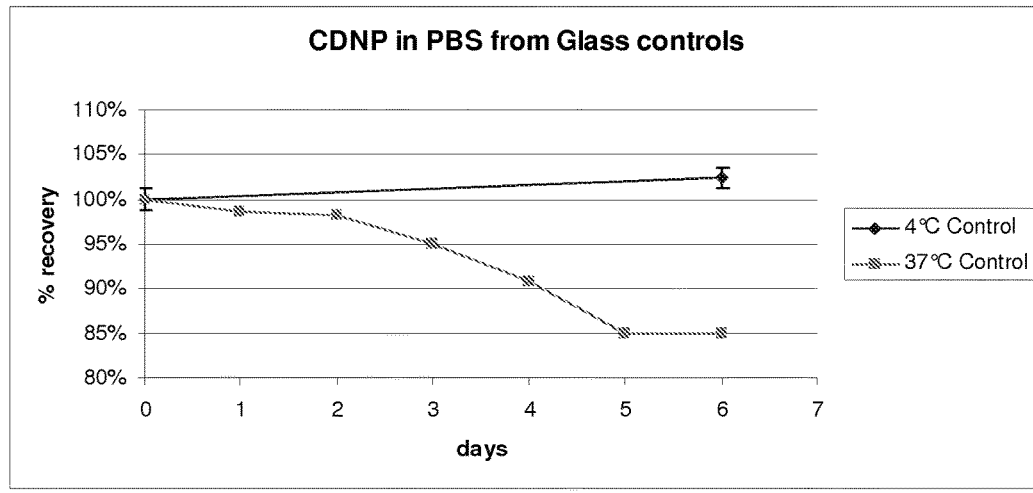
FIG. 2 shows the recovery of CD-NP stored as a 1 mg/mL solution in phosphate buffered saline (PBS).

The results for a recovery determination for 1 mg/mL CD-NP dissolved in the PBS of Example 2 are presented in Table 4 and provided in graphical form in FIG. 2. Eleven vials containing a CD-NP solution were prepared, as described in Example 4, except the CD-NP was prepared in PBS. The recovery of CD-NP from the 1 mg/mL solution was measured at 4° C. at Days 0 and 6 and from 37° C. samples collected on a daily basis (Days 1-6) and analyzed on Day 6. Recovery was calculated as a percent of the peak area (mAU) for the 4° C. control samples tested in the same HPLC run on Day 6. As shown in Table 4 and FIG. 2, the recovery of CD-NP remained stable after 6 days of storage at 4° C. The recovery of CD-NP decreased over a 6-day period of storage at 37° C. After a 6-day period of storage at 37° C., the recovery of CD-NP was about 85%.

TABLE 4

Recovery of CD-NP in PBS solution from glass vials

| Day | 4° C. % Recovery vs. average Day 0 peak area Ave ± SD (n = 5) | 37° C. % Recovery vs. Day 6 4° C. Controls |
|---|---|---|
| 0 | 100.0% ± 0.2% | 100.0% |
| 1 | n/a | 98.7% |
| 2 | n/a | 98.2% |
| 3 | n/a | 95.0% |
| 4 | n/a | 90.9% |
| 5 | n/a | 85.0% |
| 6 | 97.4% ± 1.1% | 85.0% |

Table 5 presents the results of purity determinations for 1 mg/mL CD-NP dissolved in the PBS of Example 2. As shown in Table 5, the purity of CD-NP remained relatively stable after 6 days of storage at 4° C. The purity of the same solution stored at 37° C. decreased in purity over a 6 day time period. After a 6 day period of storage at 37° C., the purity of CD-NP was about 87%.

TABLE 5

Purity of CD-NP in PBS solution from glass vials

| Day | 4° C. Glass Vial Ave ± SD, n = 5 | 37° C. Glass Vial |
|---|---|---|
| 0 | 96.56% ± 0.11% | |
| 1 | n/a | 95.22% |

TABLE 5-continued

Purity of CD-NP in PBS solution from glass vials

| Day | 4° C.<br>Glass Vial<br>Ave ± SD, n = 5 | 37° C.<br>Glass Vial |
|---|---|---|
| 2 | n/a | 92.21% |
| 3 | n/a | 91.34% |
| 4 | n/a | 90.08% |
| 5 | n/a | 89.17% |
| 6 | 96.42% ± 0.19% | 87.07% |

When stored at 37° C. in glass vials, the recovery of CD-NP decreased 15% and 8.8% in the PBS and the Tris buffer, respectively, after 6 days of storage at 37° C. A difference in CD-NP purity was also observed with a purity of 87.07% in the PBS and a purity of 91.32% in the Tris buffer after 6 days of storage at 37° C. compared to starting purities of 96.56% and 96.76%, respectively.

Example 6

Stability of 1 mg/mL CD-NP Tris Buffer Delivered from a Provisioning Apparatus

The suitability for delivery of a 1 mg/mL solution of CD-NP prepared in the Tris buffer of Example 1 was evaluated by delivery from Medtronic MiniMed® Paradigm® pumps using a MiniMed 3.0 mL reservoir (MMT-332A). Five Paradigm® pumps were prepared under identical conditions. The pump reservoirs were filled by connection to MMT-296 Quick-Set™ infusion sets and primed with the 1 mg/mL CD-NP Tris formulation. Upon filling the pumps with the formulation of CD-NP, all air bubbles were removed from the reservoirs. The solution pumped by the pumps was collected in non-vented 4 mL glass vials that were seated with Teflon™ lined septa that were pierced with Quick-Set™ infusion sets. The volume of the vials was at least 10 times the expected pumping volume so that the pressure changes in the vials were minimal and venting was unnecessary. The Paradigm® pumps containing the 1 mg/mL solution of CD-NP in the Tris buffer were equilibrated to a temperature of 37° C. to simulate conditions present due to body heat emanating from a subject and subjected to continuous agitation at 100+/−10 strokes/minute with a one inch shaking distance on an orbital shaker. The pump or provisioning apparatus was operated at a rate of 0.016 mL/hr and effluent solution collected in the 4 mL vials.

The recovery of the CD-NP solution pumped from the Paradigm® pumps was determined by comparison of the CD-NP peak area (mAU) to the mean peak area (mAU) obtained for the 4° C. glass vial control samples. Recovery is reported as a percentage of the 4° C. control peak area. Purity of the CD-NP solution pumped from the Paradigm® pumps was determined by dividing the peak area of the main chromatographic peak observed by SCX-HPLC by the sum total area of all peaks observed in the chromatogram. The content of the solution passing through the catheter was measured by SCX-HPLC in samples collected daily over a 6-day period (Days 1-6). All samples were analyzed in a single HPLC run on Day 6. The recovery and purity measured for each of the 5 pumps was averaged and a standard deviation (SD) calculated. The content of the solution remaining in the reservoir after 6 days was also evaluated for recovery and purity in the same manner (pump residual).

In certain embodiments, a therapeutic protein composition stored at a temperature from about 25 to about 45° C. for a period of 6 days has a recovery of a protein, peptide or polypeptide greater than about 90%. In certain other embodiments, a therapeutic protein composition stored at a temperature from about 25 to about 45° C. for a period of 5 days has a recovery of a protein, peptide or polypeptide greater than about 92%. In certain other embodiments, a therapeutic protein composition stored at a temperature from about 25 to about 45° C. for a period of 3 days has a recovery of a protein, peptide or polypeptide greater than about 98%.

Figure 3:
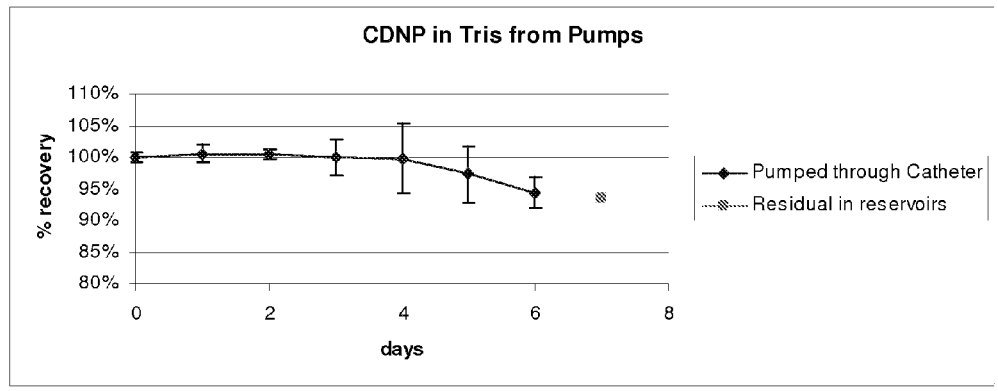
FIG. 3 shows the recovery of CD-NP stored as a 1 mg/mL solution in Tris and delivered using a provisioning apparatus.

The results for the recovery of CD-NP from the Paradigm® pumps are presented in Table 6 and FIG. 3. Measurements were taken from 5 separate Paradigm® pumps to calculate an average value and a standard deviation. Over an initial 4 day period, the recovery of CD-NP from the solution delivered by the Paradigm® pump catheter is stable at near 100%. In certain embodiments, the recovery of CD-NP after a 4 day period is about 95% or more. In other embodiments, the recovery of CD-NP after a 4 day period is about 98% or more. After 4 days, recovery was observed to decrease, but remained above about 90%. In certain embodiments, the recovery of CD-NP after a 6 day period is about 93% or more. In certain other embodiments, the recovery of CD-NP after a 6 day period is about 94% or more.

In some embodiments of the invention, a therapeutic protein composition stored and delivered by a provisioning apparatus at a temperature from about 25 to about 45° C. for a period of 4 days has a recovery of a protein, peptide or polypeptide at least about 97%. In certain other embodiments, a therapeutic protein composition stored at a temperature from about 25 to about 45° C. for a period of 6 days has a recovery of a protein, peptide or polypeptide at least about 93%. In certain other embodiments, a therapeutic protein composition stored at a temperature from about 25 to about 45° C. for a period of 6 days has a recovery of a protein, peptide or polypeptide at least about 92%.

TABLE 6

Recovery of CD-NP in Tris buffer solution from Paradigm ® pumps

| Day | % Recovered<br>vs. 4° C. Controls on Day 6<br>Ave ± SD (n = 5) |
|---|---|
| 0 | 100% ± 0.7% |
| 1 | 100.5% ± 1.4% |
| 2 | 100.5% ± 0.7% |
| 3 | 100% ± 2.9% |
| 4 | 99.8% ± 5.5% |
| 5 | 97.4% ± 4.5% |
| 6 | 94.5% ± 2.4% |
| Pump residual (Day 6) | 93.5% ± 0.2% |

The purity of the CD-NP delivered by the Paradigm® pump is presented in Table 7. Over the 6 day period of delivery at 37° C., the purity of the CD-NP was observed to decrease from 96.62% to 93.72% with the residual CD-NP solution left in the reservoir after 6 days having a purity of 93.52%. In certain embodiments, the purity of CD-NP decreases by about 5% or less over a 4 day period when delivered from a provisioning apparatus at an operating temperature from about 25 to about 45° C. In other embodiments, the purity of CD-NP decreases by about 2% or less over a 4 day period when delivered from a provisioning apparatus at an operating temperature from about 25 to about 45° C. In additional embodiments, the purity of CD-NP decreases by about 5% or less over a 6 day period when delivered from a provisioning apparatus at an operating temperature from about 25 to about 45° C., or by about 3% or less under the same conditions.

TABLE 7

Purity of CD-NP in Tris buffer solution from Paradigm ® pump

| Day | Pumped Samples Ave ± SD (n = 5) |
|---|---|
| 0 | 96.62% ± 0.14% |
| 1 | 96.29% ± 0.09% |
| 2 | 95.90% ± 0.11% |
| 3 | 95.82% ± 0.16% |
| 4 | 95.45% ± 0.22% |
| 5 | 94.97% ± 0.27% |
| 6 | 93.76% ± 0.23% |
| Pump residual (Day 6) | 93.52% ± 0.08% |

Example 7

Stability of 1 mg/mL CD-NP in PBS Delivered from a Provisioning Apparatus

The suitability for delivery of a 1 mg/mL solution of CD-NP prepared in the PBS buffer of Example 2 was evaluated by delivery from a Medtronic MiniMed Paradigm® pump using a MiniMed 3.0 mL reservoir (MMT-332A). The recovery and purity of CD-NP in PBS was evaluated in the same manner as in Example 6. Briefly, the Paradigm® pump containing the 1 mg/mL solution of CD-NP in the PBS buffer was equilibrated to a temperature of 37° C. to simulate conditions present due to body heat emanating from a subject and agitated as described. The pump or provisioning apparatus was operated at a rate of 0.016 mL/hr. The content of the solution passing through the catheter was measured by SCX-HPLC from 5 separate pumps to calculate an average value with a standard deviation (SD). The recovery of CD-NP in the solution remaining in the reservoir after 6 days was also measured.

Figure 4:
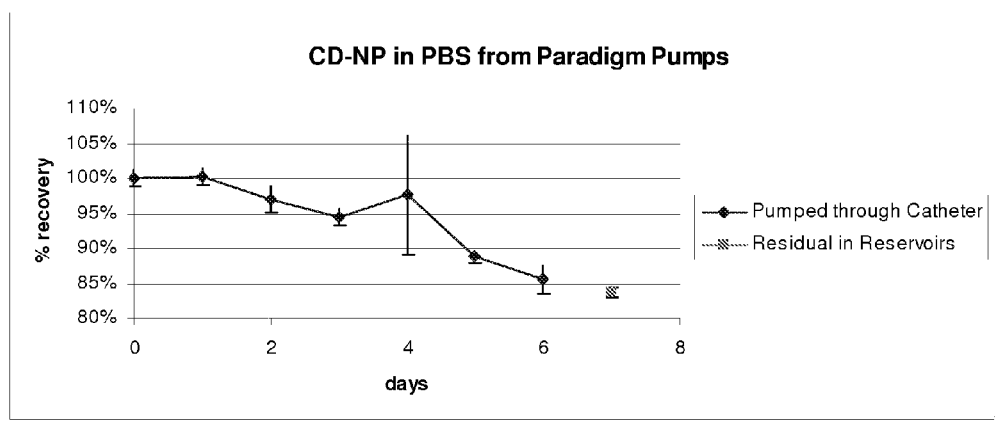
FIG. 4 shows the recovery of CD-NP stored as a 1 mg/mL solution in PBS and delivered using a provisioning apparatus.

The results for the recovery of CD-NP from the Paradigm® pump are presented in Table 8 and FIG. 4. As shown in Table 8, the 1 mg/mL CD-NP solution maintained a recovery near 100% for a period of 1 day, after which the recovery deteriorated. The recovery of CD-NP in PBS solution delivered by the Paradigm® pumps decreased from 100.2% after 1 day to 85.5% after 6 days.

TABLE 8

Recovery of CD-NP in PBS solution from Paradigm ® pump

| Day | % Recovered vs. 4° C. Controls on Day 6 Ave ± SD (n = 5) |
|---|---|
| 0 | 100% ± 1.2% |
| 1 | 100.2% ± 1.1% |
| 2 | 97% ± 1.9% |
| 3 | 94.5% ± 1.2% |
| 4 | 97.6% ± 8.4% |
| 5 | 88.8% ± 0.8% |
| 6 | 85.5% ± 2% |
| Pump residual (Day 6) | 83.7% ± 0.6% |

Table 9 reports the purity of the CD-NP in PBS solution delivered by the Paradigm® pumps. A loss in purity was observed over the course of 6 days from a purity of 96.4% to 87.0%. Purity was observed to decrease by 9.4% for CD-NP in PBS over the course of 6 days at 37° C. during delivery from the Paradigm® pumps.

TABLE 9

Purity of CD-NP in PBS solution from Paradigm ® pump

| Day | Pumped Samples Ave ± SD, n = 5 |
|---|---|
| 0 | 96.42% ± 0.19% |
| 1 | 94.84% ± 0.68% |
| 2 | 93.29% ± 0.50% |
| 3 | 91.13% ± 0.27% |
| 4 | 90.26% ± 0.29% |
| 5 | 88.58% ± 0.40% |
| 6 | 86.98% ± 0.32% |
| Pump residual (Day 6) | 86.78% ± 0.15% |

In certain embodiments, the change in relative purity of a natriuretic peptide in a composition administered by a provisioning apparatus over a course of at least 6 days is about 10% or less when at a temperature from about 25 to about 45° C. In certain other embodiments, the change in relative purity of a natriuretic peptide in a composition administered by a provisioning apparatus over a course of at least 6 days is about 5% or less when at a temperature from about 25 to about 45° C. In other embodiments, the change in relative purity of a natriuretic peptide in a composition administered by a provisioning apparatus over a course of at least 6 days is about 3% or less when at a temperature from about 25 to about 45° C.

In certain embodiments, the change in relative purity of a natriuretic peptide in a composition stored in a container or in a provisioning apparatus over a course of at least 6 days is about 10% or less when at a temperature from about 25 to about 45° C. In certain other embodiments, the change in relative purity of a natriuretic peptide in a composition stored in a container or in a provisioning apparatus over a course of at least 6 days is about 5% or less when at a temperature from about 25 to about 45° C. In other embodiments, the change in relative purity of a natriuretic peptide in a composition stored in a container or in a provisioning apparatus over a course of at least 6 days is about 3% or less when at a temperature from about 25 to about 45° C.

In certain embodiments, the pump or provisioning apparatus delivers a composition at a rate from about 0.005 to about 0.04 mL/hr. In certain other embodiments, the pump or provisioning apparatus delivers a composition at a rate from about 0.01 to about 0.025 mL/hr. In other embodiments, the pump or provisioning apparatus delivers a composition at a rate from about 0.012 to about 0.02 mL/hr.

Example 8

Stability of Biological Activity of CD-NP

The ability of a solution or formulation containing a natriuretic peptide to maintain biological activity over time while being pumped under elevated temperature and agitation was evaluated. A cell-based assay was used to measure the ability of the solution or formation to generate cGMP production.

CD-NP was prepared as a 1 mL/mg solution in the Tris buffer of Example 1 or the PBS of Example 2, as described above. Paradigm® pumps were prepared in the same manner as Examples 6 and 7 described above. Briefly, a Paradigm® pump containing the 1 mg/mL solution of CD-NP in the Tris buffer or PBS was equilibrated to a temperature of 37° C. to simulate conditions present due to body heat emanating from a subject and agitated as described. The pump or provisioning apparatus was operated at a rate of 0.016 mL/hr. The content of the solution passing through the catheter was measured using the cell-based activity cell described below.

80 µL of the Day 0 (T=0) samples from the pumps and 80 µL of the pump-delivered sample on Day 6, as described above, were aliquoted into glass vials and frozen at −80° C. until use in the cell-based assay. Human ANP (200 µg) was dissolved the day of the performance of the cell-based assay at 1 mg/mL in 200 µL PBS (Lifeline Cell Technologies) with 1% BSA. The Human ANP samples were used as a positive control. A seven point half-log dilution series of the samples was performed in PBS containing 1% BSA and 1 mM 1-methyl-3-isobutylxanthine. This created an expected concentration range from 3 nM to 3000 nM for use during cell stimulation.

Human renal medullary epithelial cells were purchased from Lifeline Cell Technologies (Walkersville, Md.). In preparation for the assay, the cells were seeded at approximately 3000 cells/cm2 and expanded to 2: 90% confluency in low serum (0.5% FBS) renal epithelial cell specific medium (Lifeline Cell Technologies). The day before performance of the cell-based assay, the cells were harvested as directed by the supplier using the supplier's trypsin and trypsin neutralizing products. The cells were seeded in 12-well plates and cultured overnight in the renal epithelial cell specific medium.

To perform the cell-based assay, the culture medium of the cells was first replaced with PBS containing 1 mM 1-methyl-3-isobutylxanthine and allowed to incubate for 10 minutes at 37° C. The stimulation of the cells for assay purposes was initiated by spiking of peptide solution into the wells. One well was used per concentration of each sample. The reported peptide concentrations were the on-plate concentrations during stimulation. The assay was terminated after 15 minutes with cell lysis buffer provided in the CatchPoint cGMP ELISA kit (Molecular Devices, Sunnyvale, Calif.).

The concentration of cGMP was measured by ELISA (CatchPoint cGMP ELISA kit). The determinations were performed in triplicate using the calibrator provided and the mean results were reported as a concentration in nM. Two ELISA plates were required to analyze the samples. The cell supernatants from the PBS and Tris formulated CD-NP samples were run on separate ELISA plates and compared against cell supernatants from the ANP control samples analyzed on the same plate.

Figure 5:
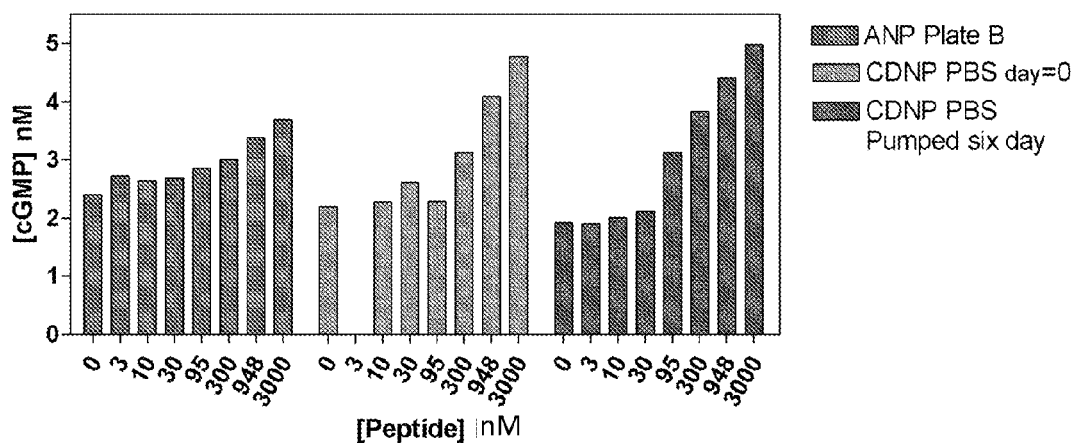
FIG. 5 shows the cGMP production in a cell-based assay for compositions having CD-NP formed in PBS and ANP controls.
Figure 6:
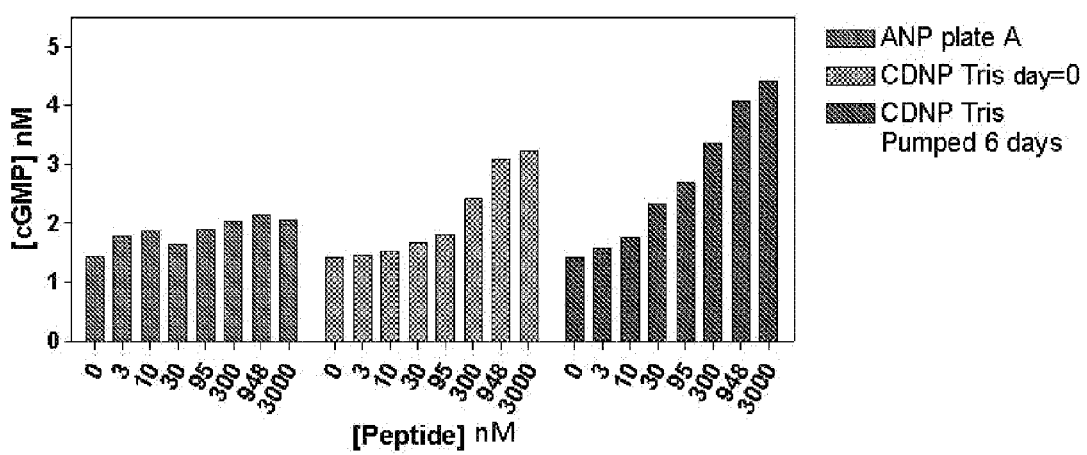
FIG. 6 shows the cGMP production in a cell-based assay for compositions having CD-NP formed in Tris and ANP controls.

The results for the whole cell stimulation of cGMP by CD-NP delivered from the Paradigm® pumps after 6 days at 37° C. are presented in FIG. 5 for the PBS formulation and in FIG. 6 for the Tris formulation. Comparison to the appropriate CD-NP formulation at Day 0 and the ANP control are also shown in FIGS. 5 and 6.

Only data collected from the same ELISA plate has been shown plotted together. The cell supernatants from the ANP samples performed differently on the two different ELISA plates. The background cGMP signal due to the basal level of cGMP present without stimulation may be masking peptide stimulation at the lower concentrations. The CD-NP Tris samples presented in FIG. 6 show a dose response in cGMP accumulation, which indicates that the cell-based assay can be a valid measure of CD-NP biological activity. Further, the level of cGMP production shown for the PBS-based CD-NP samples in FIG. 5 and the Tris-based CD-NP samples in FIG. 6 seem to be comparable.

CD-NP formulations in PBS and Tris retain biological activity could stimulate cGMP production in a whole cell assay at nM concentrations similarly before and after pump delivery. Specifically, the concentration dependent response of cGMP production is virtually unchanged between the Day 0 samples and after 6 days of pumping. These results show that there is no meaningful change in biological activity of the CD-NP peptide before and after pump delivery.

In certain embodiments, the change in the biological activity of a natriuretic peptide in a composition administered by a provisioning apparatus over a course of at least 6 days is substantially unchanged. In certain other embodiments, the change in the biological activity of a natriuretic peptide in a composition administered by a provisioning apparatus over a course of at least 6 days does not change by more than about 5%, as measured by the ability of the natriuretic peptide to stimulate cGMP production in a cell-based assay. In certain additional embodiments, the change in the biological activity of a natriuretic peptide in a composition administered by a provisioning apparatus over a course of at least 6 days does not change by more than about 5%, as measured by the ability of the natriuretic peptide to stimulate cGMP production in a cell-based assay.

What is claimed is:

1. A composition comprising:
a peptide selected from the group consisting of CD-NP (Seq. ID. No. 1), CU-NP (Seq. ID No. 4), B-CDNP (Seq. ID. No. 8), and CDNP-B (Seq. ID. No. 9), wherein the peptide is present in a concentration from about 0.05 mg/mL to about 20 mg/mL;
one or more buffers selected from the group consisting of tris(hydroxymethyl)aminomethane and a phosphate buffer, wherein the concentration of tris(hydroxymethyl)aminomethane is from about 5 to about 100 mM;
meta cresol, wherein the concentration of meta-cresol is from about 0.15 to about 0.315% by weight;
glycerol, wherein the concentration of glycerol is from about 0.1 to about 5% by weight;
and water;
wherein the composition is formed in a degassed medium; and,
wherein the composition has a pH from about 6.5 to about 7.6 when adjusted to a temperature of 25° C.

2. The composition of claim 1, wherein the composition comprises tris(hydroxymethyl)aminomethane at a concentration of about 50 mM, and meta-cresol at a concentration of about 0.25% by weight.

3. The composition of claim 2, wherein the concentration of said glycerol is about 1.6% by weight of the composition.

4. The composition of claim 3, wherein the composition has a pH of about 7.3.

5. The composition of claim 1, wherein the composition further comprises sodium chloride at a concentration from about 0.2 to about 10 grams per liter.

6. The composition of claim 5, wherein the composition comprises a phosphate buffer at a concentration from about 0.2 to about 10 grams per liter.

7. The composition of claim 1, wherein the composition is stored in a container where any headspace present has been purged with nitrogen or a noble gas to substantially remove oxygen from the headspace of the container.

8. The composition of claim 1, wherein the peptide is CD-NP (Seq. ID. No. 1).

9. The composition of claim 1, wherein the peptide is CU-NP (Seq. ID No. 4).

10. The composition of claim 1, wherein the peptide is B-CDNP (Seq. ID. No. 8).

11. The composition of claim 1, wherein the peptide is CDNP-B (Seq. ID. No. 9).

12. A composition comprising:

CD-NP (Seq. ID. No. 1), wherein CD-NP is present in a concentration from about 0.05 mg/mL to about 20 mg/mL;

one or more buffers selected from the group consisting of tris(hydroxymethyl)aminomethane and a phosphate buffer, wherein the concentration of tris(hydroxymethyl)aminomethane is from about 5 to about 100 mM;

meta cresol, wherein the concentration of meta-cresol is from about 0.15 to about 0.315% by weight;

glycerol, wherein the concentration of glycerol is from about 0.1 to about 5% by weight;

and water;

wherein the composition is formed in a degassed medium; and, wherein the composition has a pH from about 6.5 to about 7.6 when adjusted to a temperature of 25° C.

13. A composition comprising:

CU-NP (Seq. ID No. 4), wherein CU-NP is present in a concentration from about 0.05 mg/mL to about 20 mg/mL;

one or more buffers selected from the group consisting of tris(hydroxymethyl)aminomethane and a phosphate buffer, wherein the concentration of tris(hydroxymethyl)aminomethane is from about 5 to about 100 mM;

meta cresol, wherein the concentration of meta-cresol is from about 0.15 to about 0.315% by weight;

glycerol, wherein the concentration of glycerol is from about 0.1 to about 5% by weight;

and water;

wherein the composition is formed in a degassed medium; and, wherein the composition has a pH from about 6.5 to about 7.6 when adjusted to a temperature of 25° C.

* * * * *

SEQUENCE LISTING

```
<160> NUMBER OF SEQ ID NOS: 11

<210> SEQ ID NO 1
<211> LENGTH: 37
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (6)..(6)
<220> FEATURE:
<221> NAME/KEY: DISULFID
<222> LOCATION: (22)..(22)

<400> SEQUENCE: 1

Gly Leu Ser Lys Gly Cys Phe Gly Leu Lys Leu Asp Arg Ile Gly Ser
1               5                   10                  15
```

Met Ser Gly Leu Gly Cys Pro Ser Leu Arg Asp Pro Arg Pro Asn Ala
            20                  25                  30

Pro Ser Thr Ser Ala
        35

<210> SEQ ID NO 2
<211> LENGTH: 22
<212> TYPE: PRT
<213> ORGANISM: Homo sapiens
<220> FEATURE:
<221> NAME/KEY: DISULFID
<222> LOCATION: (6)..(6)
<220> FEATURE:
<221> NAME/KEY: DISULFID
<222> LOCATION: (22)..(22)

<400> SEQUENCE: 2

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 3
<211> LENGTH: 15
<212> TYPE: PRT
<213> ORGANISM: Dendroaspsis

<400> SEQUENCE: 3

Pro Ser Leu Arg Asp Pro Arg Pro Asn Ala Pro Ser Thr Ser Ala
1               5                   10                  15

<210> SEQ ID NO 4
<211> LENGTH: 32
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (11)..(11)
<220> FEATURE:
<221> NAME/KEY: DISULFID
<222> LOCATION: (27)..(27)

<400> SEQUENCE: 4

Thr Ala Pro Arg Ser Leu Arg Arg Ser Ser Cys Phe Gly Leu Lys Leu
1               5                   10                  15

Asp Arg Ile Gly Ser Met Ser Gly Leu Gly Cys Asn Ser Phe Arg Tyr
            20                  25                  30

<210> SEQ ID NO 5
<211> LENGTH: 17
<212> TYPE: PRT
<213> ORGANISM: Homo sapiens

<400> SEQUENCE: 5

Cys Phe Gly Leu Lys Leu Asp Arg Ile Gly Ser Met Ser Gly Leu Gly
1               5                   10                  15

Cys

<210> SEQ ID NO 6
<211> LENGTH: 10
<212> TYPE: PRT
<213> ORGANISM: Homo sapiens

```
<400> SEQUENCE: 6

Thr Ala Pro Arg Ser Leu Arg Arg Ser Ser
1               5                   10

<210> SEQ ID NO 7
<211> LENGTH: 5
<212> TYPE: PRT
<213> ORGANISM: Homo sapiens

<400> SEQUENCE: 7

Asn Ser Phe Arg Tyr
1               5

<210> SEQ ID NO 8
<211> LENGTH: 37
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (6)..(6)
<220> FEATURE:
<221> NAME/KEY: DISULFID
<222> LOCATION: (22)..(22)

<400> SEQUENCE: 8

Gly Leu Ser Lys Gly Cys Phe Gly Arg Lys Met Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
        35

<210> SEQ ID NO 9
<211> LENGTH: 37
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (6)..(6)
<220> FEATURE:
<221> NAME/KEY: DISULFID
<222> LOCATION: (22)..(22)

<400> SEQUENCE: 9

Gly Leu Ser Lys Gly Cys Phe Gly Leu Lys Leu Asp Arg Ile Ser Ser
1               5                   10                  15

Ser Ser Gly Leu Gly Cys Pro Ser Leu Arg Asp Pro Arg Pro Asn Ala
            20                  25                  30

Pro Ser Thr Ser Ala
        35

<210> SEQ ID NO 10
<211> LENGTH: 37
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (6)..(6)
<220> FEATURE:
<221> NAME/KEY: MISC_FEATURE
<222> LOCATION: (9)..(10)
```

```
<223> OTHER INFORMATION: X is selected from Lys, Arg and His
<220> FEATURE:
<221> NAME/KEY: MISC_FEATURE
<222> LOCATION: (11)..(11)
<223> OTHER INFORMATION: X is selected from Leu, Ile, Met, Val and Ala
<220> FEATURE:
<221> NAME/KEY: DISULFID
<222> LOCATION: (22)..(22)

<400> SEQUENCE: 10

Gly Leu Ser Lys Gly Cys Phe Gly Xaa Xaa Xaa Asp Arg Ile Gly Ser
1               5                   10                  15

Met Ser Gly Leu Gly Cys Pro Ser Leu Arg Asp Pro Arg Pro Asn Ala
            20                  25                  30

Pro Ser Thr Ser Ala
            35

<210> SEQ ID NO 11
<211> LENGTH: 37
<212> TYPE: PRT
<213> ORGANISM: Artificial Sequence
<220> FEATURE:
<223> OTHER INFORMATION: artificial peptide construct
<220> FEATURE:
<221> NAME/KEY: DISULFID
<222> LOCATION: (6)..(6)
<220> FEATURE:
<221> NAME/KEY: MISC_FEATURE
<222> LOCATION: (15)..(17)
<223> OTHER INFORMATION: X is selected from Ser, Gly, Ala and Thr
<220> FEATURE:
<221> NAME/KEY: DISULFID
<222> LOCATION: (22)..(22)

<400> SEQUENCE: 11

Gly Leu Ser Lys Gly Cys Phe Gly Leu Lys Leu Asp Arg Ile Xaa Xaa
1               5                   10                  15

Xaa Ser Gly Leu Gly Cys Pro Ser Leu Arg Asp Pro Arg Pro Asn Ala
            20                  25                  30

Pro Ser Thr Ser Ala
            35
```